(12) United States Patent
Choi et al.

(10) Patent No.: US 7,999,151 B2
(45) Date of Patent: Aug. 16, 2011

(54) METHOD OF PRODUCING ASTAXANTHIN OR METABOLIC PRODUCT THEREOF BY USING CAROTENOID KETOLASE AND CAROTENOID HYDROXYLASE GENES

(75) Inventors: Seon-Kang Choi, Gangneung (KR); Norihiko Misawa, Kamaishi (JP)

(73) Assignee: Kirin Holdings Kabushiki Kaisha, Tokyo (JP)

( * ) Notice: Subject to any disclaimer, the term of this patent is extended or adjusted under 35 U.S.C. 154(b) by 1158 days.

(21) Appl. No.: 11/597,362

(22) PCT Filed: May 26, 2005

(86) PCT No.: PCT/JP2005/009609
§ 371 (c)(1), (2), (4) Date: Apr. 12, 2007

(87) PCT Pub. No.: WO2005/118812
PCT Pub. Date: Dec. 15, 2005

(65) Prior Publication Data
US 2009/0298146 A1     Dec. 3, 2009

(30) Foreign Application Priority Data

Jun. 4, 2004 (JP) .................................. 2004-166625

(51) Int. Cl.
*C12N 1/21* (2006.01)
*C12N 15/31* (2006.01)
*C12N 15/52* (2006.01)
*C12N 15/70* (2006.01)
*C12N 15/82* (2006.01)
*A01H 5/00* (2006.01)

(52) U.S. Cl. ........ 800/288; 800/282; 800/298; 435/419; 435/468; 435/252.33

(58) Field of Classification Search .......... None
See application file for complete search history.

(56) References Cited

U.S. PATENT DOCUMENTS

| | | | |
|---|---|---|---|
| 5,811,273 | A | 9/1998 | Misawa et al. |
| 5,910,433 | A | 6/1999 | Kajiwara et al. |
| 2004/0078846 | A1 | 4/2004 | Desouza et al. |

FOREIGN PATENT DOCUMENTS

| | | |
|---|---|---|
| EP | 1 693 377 A1 | 8/2006 |
| WO | WO-95/18220 A1 | 7/1995 |
| WO | WO 02/079395   * | 10/2002 |
| WO | WO-02/079395 A2 | 10/2002 |
| WO | WO-03/080849 A2 | 10/2003 |
| WO | WO-2004/017749 A2 | 3/2004 |
| WO | WO-2004/018693 A2 | 3/2004 |
| WO | WO-2004/018695 A2 | 3/2004 |
| WO | WO-2005/049643 A1 | 6/2005 |
| WO | WO-2005/062867 A2 | 7/2005 |

OTHER PUBLICATIONS

Masawa et al. Plant Cell Physiology(1998); 39(5): 560-564.*
Mann V. et al. Nature Biotechnology vol. 18 Aug. 2000 pp. 888-892.*
Kajiwara S. et al. Plant Molecular Biology; Oct. 1995, vol. 29 pp. 343-352.*
Nishida, Y. et al. Applied and Environmental Microbiology; Aug. 2005, pp. 4286-4296.*
Fraser et al., European Journal of Biochemistry, vol. 252, No. 2, Jan. 1998, pp. 229-236, XP-000915404.
Nishida et al., Nihon Nogei Kagakukai 2004 Nendo Taikai Koen Yoshishu, Mar. 5, 2004, p. 137 (3A01p17).
Komemushi et al., Nihon Nogei Kagakukai 2004 Nendo Taikai Koen Yoshishu, Mar. 5, 2004, p. 137 (3A01p18).
Kajiwara et al., Plant Mol. Biol. 1995, vol. 29, pp. 343-352.
Stalberg et al., Plant J., 2003, vol. 36, pp. 771-779.
Mann et al., Nature Biotechnology, 2000, vol. 18, No. 8, pp. 888-892.
Sai et al., Dai 7 Kai Japanese Society for Marine Biotechnology Taikai Koen Yoshishu, Jun. 17, 2004, p. 118 (AO-7).

* cited by examiner

*Primary Examiner* — Russell Kallis
(74) *Attorney, Agent, or Firm* — Birch, Stewart, Kolasch & Birch, LLP.

(57) ABSTRACT

To provide a microorganism or a plant transformed with a β-ionone ring-4-ketolase gene and/or β-ionone ring-3-hydroxylase gene derived from *Brevundimonas* sp. strain SD-212. The β-ionone ring-4-ketolase gene and β-ionone ring-3-hydroxylase gene produced by *Brevundimonas* sp. strain SD-212 each have a high activity compared with those of known enzymes, and therefore microorganisms transformed with the genes encoding these enzymes can efficiently produce astaxanthin.

9 Claims, 6 Drawing Sheets

METHOD OF PRODUCING ASTAXANTHIN OR METABOLIC PRODUCT THEREOF BY USING CAROTENOID KETOLASE AND CAROTENOID HYDROXYLASE GENES

This application is a National Stage Application under 35 U.S.C. §371(c) of PCT Application No. PCT/JP2005/009609, filed May 26, 2005, which claims the priority of Japanese Patent Application No. 2004-166625 filed Jun. 4, 2004. The entire disclosure and contents of the above applications are hereby incorporated by reference herein.

TECHNICAL FIELD

The present invention relates to a method for preparing astaxanthin or metabolites thereof by using a microorganism or a plant transformed with an oxygenase gene encoding an enzyme that replaces a methylene group at the position 4 (4') of a β-ionone ring (β ring) of a carotenoid with a keto group or a hydroxylase gene encoding an enzyme that introduces a hydroxyl group at the position 3 (3') carbon of a β-ionone ring (β ring) of a carotenoid.

BACKGROUND ART

Carotenoid (also called "carotinoid") is a general term for pigments occurring abundantly in nature and is built up from an isoprene backbone of 40 carbon atoms. To date, more than 600 species of carotenoids have been isolated (Pfander, H., ed., Key to Carotenoids, Birkhauser, Basel, 1987). Recently, prophylactic effects of carotenoids on various chronic diseases such as cancer have been recognized, and a great number of reports have been made (see, for example, Nishino, H., Murakoshi, M., Yano, M. Food Style 21, 4, 53-55, 2000; Nishino, H. et al, Carotenoids in cancer chemoprevention, Cancer Metastasis Rev. 21, 257-264, 2002; Mayne, S. T., β-Carotene, carotenoids, and disease prevention in humans, FASEB J., 10, 690-701, 1996). Among them, astaxanthin is a carotenoid that has been particularly recognized as a material for health foods, recently (Uonomi, T., Antioxidant effect and cancer-metastasis-suppressive effect of, the greatest carotenoid of all time, "astaxanthin", Food Style 21, 4, 70-75, 2000). In vitro evaluation of astaxanthin for elimination effect against singlet oxygen, which is one type of active oxygen, shows that the effect of astaxanthin is 500 times that of vitamin E, 40 times that of β-carotene, and 10 times that of lycopene. Further, in epidemiological and clinical studies of human subjects, it has been observed that astaxanthin suppresses oxidation of blood LDL and thereby suppresses arteriosclerosis (the above-mentioned document: Uonomi, T. Food Style 21, 4, 70-75, 2000). In addition, it has been revealed that astaxanthin enhances NK cell activity and has effects on preventing cataract, age-related macular degeneration, and bladder cancer (the above-mentioned document: Food Style 21, 4, 70-75, 2000; Tanaka, T. et al, Chemoprevention of mouse urinary bladder carcinogenesis by the naturally occurring carotenoid astaxanthin, Carcinogenesis 15, 15-19, 1994).

Astaxanthin is commercially prepared by being extracted from crustacea such as euphausiid and crawfish, and is also extracted from a culture of astaxanthin-producing green algae *Haematococcus pluvialis*. However, in the former case, astaxanthin has disadvantages in quality and cost, namely, unevenness in pigment concentration, an odor peculiar to raw materials, and a low yield. In the latter case, astaxanthin cannot be stably produced because of the requirement of culturing for a long time at an intermediate temperature at a neutral pH. Thus, to date, stable supply of inexpensive astaxanthin has not been realized. Therefore, the stable supplying of inexpensive astaxanthin may allow various new physiological tests for evaluating the advantageous effects of astaxanthin on human health to be conducted. Consequently, the present health food market will be significantly expanded.

In order to achieve the above-mentioned object, astaxanthin may be commercially supplied by engineering a recombinant microorganism or plant that can produce a large amount of astaxanthin through metabolic engineering. Genes allowing a microorganism or a plant to produce astaxanthin have already been obtained. It has been possible to make a microorganism such as bacteria or yeast or a specific organ of a plant that does not originally produce carotenoids to synthesize astaxanthin by using these genes (Non-Patent Document 1: Miura, Y., Kondo, K., Saito, T., Shimada, H., Fraser. P. D., and Misawa, N., Production of the carotenoids, lycopene, β-carotene, and astaxanthin in the food yeast *Candida utilis*. Appl. Environ. Microbiol. 64, 1226-1229, 1998; Mann, V., Harker, M., Pecker, I., and Hirschberg, J., Metabolic engineering of astaxanthin production in tobacco flowers, Nat. Biotechnol. 18, 888-892, 2000). However, when all genes necessary for synthesizing astaxanthin are actually introduced and expressed, a large amount of biosynthetic intermediates of astaxanthin are accumulated in addition to astaxanthin as the end product. These intermediates are carotenoids that are biosynthetic intermediates produced in the pathways from β-carotene to astaxanthin (see FIG. 1). These pathways are rate-determining steps of astaxanthin synthesis. In an example using a recombinant *Escherichia coli*, in addition to astaxanthin (36 to 50%) as the end product, biosynthetic intermediates such as adonixanthin (4-ketozeaxanthin), adonirubin (phoenicoxanthin), canthaxanthin, 3-hydroxyechinenone, 3'-hydroxyechinenone were detected (Non-Patent Document 1). Recently, a β-ionone ring-4-ketolase (β-C4-ketolase) gene (crtO) derived from *Haematococcus pluvialis* has been introduced into *Arabidopsis* and expressed in the seeds. However, all carotenoids mainly produced were biosynthetic intermediates (adonirubin, canthaxanthin, and the like) of astaxanthin. It has been revealed that two enzymes, i.e., β-ionone ring-3-hydroxylase (β-C3-hydroxylase) (CrtZ) and β-ionone ring-4-ketolase (β-C4-ketolase) (CrtW, CrtO, or Bkt), are responsible for the synthesis pathway from β-carotene to astaxanthin (see FIG. 1). Therefore, the efficiencies of these two enzymes have been desired to be increased for accelerating the production of astaxanthin. For example, the efficiency of β-ionone ring-4-ketolase of converting adonixanthin into astaxanthin is particularly low, and therefore adonixanthin is accumulated in many cases (Non-Patent Document 2: Yokoyama, A. and Miki, W., Composition and presumed biosynthetic pathway of carotenoids in the astaxanthin-producing bacterium *Agrobacterium aurantiacum*, FEMS Microbiol. Lett. 128, 139-144, 1995).

Non-Patent Document 1: Misawa, N., Satomi, Y., Kondo, K., Yokoyama, A., Kajiwara, S., Saito, T., Ohtani, T., and Miki, W., Structure and functional analysis of a marine bacterial carotenoid biosynthesis gene cluster and astaxanthin biosynthetic pathway proposed at the gene level, J. Bacteriol. 177, 6575-6584, 1995.

Non-Patent Document 2: Fraser, P. D., Shimada, H., and Misawa, N., Enzymic confirmation of reactions involved in routes to astaxanthin formation, elucidated using a direct substrate in vitro assay, Eur. J. Biochem. 252, 229-236, 1998.

DISCLOSURE OF THE INVENTION

Problems to be Solved by the Invention

An object of the present invention is to provide a method for efficiently producing astaxanthin or metabolites thereof by using a recombinant microorganism or a plant, which is transformed with genes encoding an enzyme that replaces a methylene group at the position 4 of a β-ionone ring with a keto group [β-ionone ring-4-ketolase (β-C4-ketolase); carotenoid 4,4'-β-oxygenase] or an enzyme that introduces a hydroxyl group at the position 3 carbon of a β-ionone ring [β-ionone ring-3-hydroxylase (β-C3-hydroxylase); carotenoid 3,3'-β-hydroxylase] and expresses such genes.

Means for Solving the Problem

The present inventors have focused on the fact that though a marine bacterium *Brevundimonas* sp. strain SD-212 (MBIC 03018) is capable of producing astaxanthin and metabolites thereof, properties of its carotenoid biosynthesis enzyme have not been revealed yet. The present inventors have conducted intensive studies and, as a result, have found that an oxygenase cloned from the marine bacterium and being capable of replacing a methylene group at the position 4 of a β-ionone ring with a keto group [CrtW: β-ionone ring-4-ketolase (β-C4-ketolase); carotenoid 4,4'-β-oxygenase] can efficiently synthesize astaxanthin from adonixanthin. In addition, the present inventors have found that a hydroxylase cloned from the marine bacterium and being capable introducing a hydroxyl group at the position 3 carbon of a β-ionone ring [CrtZ: β-ionone ring-3-hydroxylase (β-C3-hydroxylase); carotenoid 3,3'-β-hydroxylase] synthesizes astaxanthin more efficiently than the same enzyme (CrtZ) derived from other bacteria.

First, a cosmid library was prepared in *E. coli* using the chromosomal DNA of *Brevundimonas* sp. strain SD-212. Subsequently, PCR primers were designed based on the finding that phytoene desaturase (crtI) genes had two conserved domains among carotenoid-producing bacteria. Using the resultant primers, PCR was performed with the chromosomal DNA of *Brevundimonas* sp. strain SD-212 as a template. As a result, a 1.1-kb DNA fragment was amplified. The nucleotide sequence of this fragment was determined and found to be a partial sequence of crtI. Colony hybridization of strain SD-212 cosmid library was performed with the crtI partial sequence fragment as a probe. Several positive colonies were obtained. Plasmid DNA was prepared from the positive colonies and subjected to Southern hybridization, to thereby obtain a positive 12-kb EcoRI DNA fragment. The nucleotide sequence of this 12-kb EcoRI fragment was determined, and thereby it has been confirmed that a carotenoid biosynthesis gene cluster [seven open reading frames (ORFs) having homology to existing crt genes (6 genes) including crtW and crtZ, and idi gene (one gene)] is present within this fragment. Then, for forced expression of the crtW gene derived from the strain in *E. coli* by the fusion protein method using the lac promoter in *E. coli* vector pUC18 and a LacZ leader sequence, constructs were prepared. Similarly, constructs of two crtW genes derived from *Paracoccus* sp. were prepared as controls. Then, using an *Erwinia*-derived crt gene cluster (crtE, crtB, crtI, crtY, and crtZ), functional analysis of various types of CrtWs was performed in host *E. coli* cells producing zeaxanthin. The results revealed that CrtW derived from *Brevundimonas* sp. strain SD-212 can efficiently convert adonixanthin into astaxanthin and thereby can efficiently synthesize astaxanthin. In addition, for forced expression of the crtZ gene derived from the strain in *E. coli* by the fusion protein method using the lac promoter in *E. coli* vector pUC18 and a LacZ leader sequence, constructs were prepared. Similarly, constructs of two crtZ genes derived from *Paracoccus* sp. were prepared as controls. Further, constructs of crtZs derived from *Erwinia* sp. and *Flavobacterium* sp. strain P99-3 were similarly prepared. However, in a case of the latter ctrZ of the strain P99-3, pUC8 was used instead of pUC18. Then, using an *Erwinia*-derived crt gene cluster (crtE, crtB, crtI, and crtY) and a *Paracoccus*-derived crtW gene, functional analysis of various types of CrtZs was performed in host *E. coli* cells producing canthaxanthin. The results revealed that when the CrtZ derived from *Brevundimonas* sp. strain SD-212 was used, the amount of produced astaxanthin was the highest, namely, this CrtZ can most efficiently synthesize astaxanthin. Thus, the present invention has been accomplished.

The present invention provides the following (1) to (12):

(1) A microorganism or a plant transformed with a ionone ring-4-ketolase gene encoding (a) a peptide including an amino acid sequence set forth in SEQ ID NO: 2; (b) a peptide including an amino acid sequence derived from the amino acid sequence set forth in SEQ ID NO: 2 by addition, deletion, or substitution of one or more amino acids and having a β-ionone ring-4-ketolase activity; or (c) a bacterium-derived peptide encoded by DNA including a nucleotide sequence set forth in SEQ ID NO: 1 or DNA that hybridizes to DNA complementary to the DNA including the nucleotide sequence set forth in SEQ ID NO: 1 under stringent conditions and having a β-ionone ring-4-ketolase activity, wherein the microorganism or the plant is capable of synthesizing astaxanthin or metabolites thereof;

(2) The microorganism or the plant according to the above (1), wherein the microorganism or the plant is transformed by introducing a β-ionone ring-4-ketolase gene with other carotenoid biosynthesis genes thereinto;

(3) The microorganism or the plant according to the above (2), wherein the other carotenoid biosynthesis genes may be all or a part of a gene cluster required for synthesizing a carotenoid containing a β-ionone ring that is hydroxylated at the position 3, from farnesyl pyrophosphate;

(4) The microorganism according to any one of the above (1) to (3), wherein the microorganism is *Escherichia coli*;

(5) A method for preparing astaxanthin or metabolites thereof, the method including the steps of culturing the microorganism according to any one of the above (1) to (4) in a medium and obtaining astaxanthin or metabolites thereof from the culture or cells;

(6) A method for preparing astaxanthin or metabolites thereof, the method including the steps of cultivating the plant according to any one of the above (1) to (3) and obtaining astaxanthin or metabolites thereof from the plant;

(7) A microorganism or a plant transformed with a β-ionone ring-3-hydroxylase gene encoding (d) a peptide including an amino acid sequence set forth in SEQ ID NO: 10; (e) a peptide including an amino acid sequence derived from the amino acid sequence set forth in SEQ ID NO: 10 by addition, deletion, or substitution of one or more amino acids and having a β-ionone ring-3-hydroxylase activity; or (f) a bacterium-derived peptide encoded by DNA including a nucleotide sequence set forth in SEQ ID NO: 9 or DNA that hybridizes to DNA complementary to the DNA including the nucleotide sequence set forth in SEQ ID NO: 9 under stringent conditions and having a β-ionone ring-3-hydroxylase activity, wherein the microorganism or the plant is capable of synthesizing astaxanthin or metabolites thereof;

(8) The microorganism or the plant according to the above (7), wherein the microorganism or the plant is transformed by introducing a β-ionone ring-3-hydroxylase gene with other carotenoid biosynthesis genes thereinto;

(9) The microorganism or the plant according to the above (8), wherein the other carotenoid biosynthesis genes may be all or a part of a gene cluster required for synthesizing a carotenoid having a β-ionone ring that contains a keto group at the position 4, from farnesyl pyrophosphate;

(10) The microorganism according to any one of the above (7) to (9), wherein the microorganism is *Escherichia coli*;

(11) A method for preparing astaxanthin or metabolites thereof, the method including the steps of culturing the microorganism according to any one of the above (7) to (10) in a medium and obtaining astaxanthin or metabolites thereof from the culture or cells; and

(12) A method for preparing astaxanthin or metabolites thereof, the method including the steps of cultivating the plant according to any one of the above (7) to (9) and obtaining astaxanthin or metabolites thereof from the plant.

The present invention will now be described in detail.

1. Marine Bacterium *Brevundimonas* sp. Strain SD-212 (MBIC 03018) as a Gene Source The marine bacterium *Brevundimonas* sp. strain SD-212 (SD212; MBIC 03018) is a source of genes of interest and is α-proteobacterium isolated from the seawater around Volcano Islands. The GC content is 67.1 (mol) %. Yokoyama et al. of Marine Biotechnology Institute Co., Ltd. have reported that carotenoids produced by this marine bacterium include astaxanthin, 2-hydroxyastaxanthin, and 2-hydroxyadanixanthin (see Yokoyama, A., Miki, W., Izumida, H., and Shizuri, Y., New trihydroxy-keto-carotenoids isolated from an astaxanthin-producing marine bacterium. Biosci. Biotech. Bioche. 60, 200-203, 1996). This bacterium is available from Marine Biotechnology Institute Co., Ltd. under No. MBIC 03018. The 16S rDNA sequence and gyrB gene sequence of this bacterium are registered at GenBank/DDBJ under Accession Nos. AB016849 and AB014993, respectively.

2. Gene Encoding β-Ionone Ring-4-Ketolase

In the present invention, a gene encoding the following peptides (a), (b), or (c) (hereinafter, sometimes referred to as "crtW gene of the present invention") is used:

(a) a peptide including an amino acid sequence set forth in SEQ ID NO: 2;

(b) a peptide including an amino acid sequence derived from the amino acid sequence set forth in SEQ ID NO: 2 by addition, deletion, or substitution of one or more amino acids and having a β-ionone ring-4-ketolase activity; and (c) a bacterium-derived peptide encoded by DNA including a nucleotide sequence set forth in SEQ ID NO: 1 or DNA that hybridizes to DNA complementary to the DNA including the nucleotide sequence set forth in SEQ ID NO: 1 under stringent conditions and having a β-ionone ring-4-ketolase activity.

The peptide (a) is a *Brevundimonas* sp. strain SD-212-derived peptide (sometimes referred to as CrtW) having a β-ionone ring-4-ketolase activity and consisting of a 244-amino-acid sequence.

The peptide (b) is a peptide derived from the peptide (a) by mutation within a range not to cause the elimination of the efficient β-ionone ring-4-ketolase activity. The mutation includes artificial mutations as well as spontaneous mutations. The artificial mutations may be introduced by a site-specific mutagenesis method (Nucleic Acids Res. 10, 6487-6500, 1982), but the method is not limited to this. The number of mutated amino acids is not particularly limited as long as the β-ionone ring-4-ketolase activity is retained. Usually, the number of mutated amino acids is within 20, preferably within 10, and more preferably within 5.

The peptide (c) is a bacterium-derived peptide obtained by DNA hybridization and has a β-ionone ring-4-ketolase activity. The "stringent conditions" in the definition of the peptide (c) are conditions allowing specific hybridization but not allowing non-specific hybridization. Generally, such conditions are about "0.5×SSC, 0.1% SDS, 42° C.", and preferably about "0.2×SSC, 0.1% SDS, 65° C.". The DNA obtained by the hybridization generally has a high homology to the DNA represented by the nucleotide sequence set forth in SEQ ID NO: 1. The term "high homology" refers to a 75% or more homology, and preferably a 90% or more homology.

The crtW gene of the present invention may be obtained, for example, as described below. First, a cosmid library of the marine bacterium Brevundimonas sp. strain SD-212 is prepared in *E. coli*. Then, the gene of the present invention can be obtained by a colony hybridization method using a homologous sequence of a carotenoid biosynthesis gene as described in Example 6 or a PCR cloning method.

3. Gene Encoding β-Ionone Ring-3-Hydroxylase

In the present invention, a gene encoding the following peptides (d), (e), or (f) (hereinafter, sometimes referred to as "crtZ gene of the present invention") is used:

(d) a peptide including an amino acid sequence set forth in SEQ ID NO: 10;

(e) a peptide including an amino acid sequence derived from the amino acid sequence set forth in SEQ ID NO: 10 by addition, deletion, or substitution of one or more amino acids and having a β-ionone ring-3-hydroxylase activity; and (f) a bacterium-derived peptide encoded by DNA including a nucleotide sequence set forth in SEQ ID NO: 9 or DNA that hybridizes to DNA complementary to the DNA including the nucleotide sequence set forth in SEQ ID NO: 9 under stringent conditions and having a β-ionone ring-3-hydroxylase activity.

The peptide (d) is a *Brevundimonas* sp. strain SD-212-derived peptide (sometimes referred to as CrtZ) having a β-ionone ring-3-hydroxylase activity and consisting of a 161-amino-acid sequence.

The peptide (e) is a peptide derived from the peptide (d) by mutation within a range not to cause the elimination of the efficient β-ionone ring-3-hydroxylase activity. The "mutation" is the same as in the above-described crtW gene of the present invention.

The peptide (f) is a bacterium-derived peptide obtained by DNA hybridization and has a β-ionone ring-3-hydroxylase activity. The "stringent conditions" in the definition of the peptide (f) are the same as in the above-described crtW gene of the present invention.

The crtZ gene of the present invention may be obtained, for example, as described below. First, a cosmid library of the marine bacterium *Brevundimonas* sp. strain SD-212 is prepared in *E. coli*. Then, the gene of the present invention can be obtained by a colony hybridization method using a homologous sequence of a carotenoid biosynthesis gene as described in Example 6 or a PCR cloning method.

The crtW gene and the crtZ gene according to the present invention are contained in a 12-kb EcoRI DNA fragment containing a carotenoid biosynthesis gene cluster of *Brevundimonas* sp. strain SD-212. *Escherichia coli* carrying a plasmid p5Bre2-15 obtained by inserting the DNA fragment into *E. coli* vector pBluescript II KS— has been deposited at the International Patent Organism Depository, National Institute of Advanced Industrial Science and Technology under the Accession No. P-19580.

4. Microorganism or Plant Producing Astaxanthin or Metabolites Thereof

The present invention includes a microorganism or a plant transformed with the crtW gene described in the above 2, and a microorganism or a plant transformed with the crtZ gene described in the above 3. The microorganism or the plant is often transformed so as to carry not only the gene of the invention but also another carotenoid biosynthesis gene, but when the microorganism or the organ to be expressed in the plant inherently produces a carotenoid serving as a substrate, the another carotenoid biosynthesis gene may not be introduced or may be partially introduced.

Examples of host microorganisms include, but not limited to, E. coli. Examples of host plants include, but not limited to, rapeseed.

In general, the another carotenoid biosynthesis gene may be all or a part of a gene cluster required for synthesizing β-carotene from farnesyl pyrophosphate (FPP). Examples of such a gene cluster include a crtE gene encoding an enzyme that synthesizes geranylgeranyl pyrophosphate (GGPP) from FPP, a crtB gene encoding an enzyme that synthesizes phytoene from two molecules of GGPP, a crtI gene encoding an enzyme that synthesizes lycopene from phytoene, and a crtY gene (usually, derived from *Erwinia* bacteria) encoding an enzyme that synthesizes β-carotene from lycopene. In order to synthesize astaxanthin from β-carotene, it is preferable to use both the crtW gene and the crtZ gene according to the present invention. However, only either one of them may be used. When the crtW gene according to the present invention is used alone, it is necessary to use a crtZ gene derived from another organism (usually, *Erwinia* sp. or *Paracoccus* sp.) or an equivalent gene thereof for introducing a hydroxyl group at the position 3 (3') of β-carotene. When the crtZ gene according to the present invention is used alone, it is necessary to use a crtW gene derived from another organism (usually, *Paracoccus* sp.) or an equivalent gene thereof for introducing a keto group at the position 4 (4') of β-carotene.

When all or a part of the other carotenoid biosynthesis gene cluster is inserted into an appropriate expression vector and then introduced into a host microorganism employed for expression, the recombinant microorganism begins to produce a β-ionone ring-containing carotenoid (β-carotene or its metabolite), a 3-hydroxy-β-ionone ring-containing carotenoid (zeaxanthin or its metabolite), or a 4-keto-β-ionone ring-containing carotenoid (canthaxanthin or its metabolite). (Every microorganism is capable of producing the substrate FPP. Although some microorganisms produce only a small amount of GGPP, every microorganism is capable of producing GGPP.)

With respect to a plant, when a part of the above-mentioned gene cluster is inserted into an appropriate vector for plant transformation by using a promoter (for example, a napin promoter for expression in seeds) to be expressed in an organ employed for expression and a transit peptide (for example, Rubisco small subunit transit peptide) directing a plastid such as a chloroplast and then introduced into a plant, the recombinant plant begins to produce a β-ionone ring-containing carotenoid (β-carotene or its metabolite), a 3-hydroxy-β-ionone ring-containing carotenoid (zeaxanthin or its metabolite), or a 4-keto-β-ionone ring-containing carotenoid (canthaxanthin or its metabolite). In general, many plant organs that produce plant carotenoids, for example, rapeseed seeds, have most of genes necessary for producing β-ionone ring-containing carotenoids. However, by the introduction and expression of the crtB gene, the amount of carotenoids production is possibly increased. (Shewmaker, C. K. et al., Seed-specific overexpression of phytoene synthase: increase in carotenoids and other metabolic effects. Plant J. 20, 401-412, 1999).

When the crtW gene and/or the crtZ gene (when the host is a plant, the above-mentioned transit peptide sequence is necessarily linked to the N-terminal sequence) according to the present invention is further introduced to and expressed in the thus prepared recombinant microorganism or plant producing a β-ionone ring-containing carotenoid (β-carotene or its metabolite), a 3-hydroxy-β-ionone ring-containing carotenoid (zeaxanthin or its metabolite), or a 4-keto-β-ionone ring-containing carotenoid (canthaxanthin or its metabolite), the microorganism or the plant begins to produce astaxanthin that is a carotenoid in which a methylene group at the position 4 (4') of β-carotene is replaced with a keto group and a hydroxyl group is introduced at the position 3 (3') carbon of β-carotene, in which a methylene group at the position 4 (4') of zeaxanthin is replaced with a keto group, or in which a hydroxyl group is introduced at the position 3 (3') carbon of canthaxanthin, or produce astaxanthin metabolites (for example, 2-hydroxyastaxanthin and esters of astaxanthin) converted by an astaxanthin-metabolizing endogenous enzyme.

Information about vectors of various microorganisms such as *E. coli* and yeast, and methods of introduction and expression of exogenous genes are disclosed in a large number of experimental manuals (for example, Sambrook, J., Russel, D. W., Molecular Cloning, A Laboratory Manual, $3^{rd}$ Edition, CSHL Press, 2001). Selection of vectors and introduction and expression of genes may be performed according to these manuals.

Information about vectors for plant transformation and methods of introduction and expression of exogenous genes are disclosed in a large number of experimental manuals (for example, Ishida, I., Misawa, N., Saibo Kogaku Jikken Sosa Nyumon (The handbook for the cell engineering experimental manipulation), Kodansha Scientific, 1992). Selection of vectors and introduction and expression of genes may be performed according to these manuals.

4. Method of Preparing Astaxanthin or Metabolites Thereof

The present invention provides a method of efficiently preparing astaxanthin or metabolites thereof by culturing the above-described microorganism in a medium and obtaining astaxanthin or metabolites thereof from the culture or cells. In addition, the present invention also provides a method of efficiently preparing astaxanthin or metabolites thereof by cultivating the above-described plant and obtaining astaxanthin or metabolites thereof from an organ, such as a seed, of the plant.

Examples of the astaxanthin metabolites include, but not limited to, 2-hydroxyastaxanthin and esters of astaxanthin. Furthermore, there are cases that astaxanthin metabolites are not produced.

The SEQ ID NOS in the SEQUENCE LISTING of the present specification represent the following sequences:

SEQ ID NO: 1: nucleotide sequence of the crtW gene of *Brevundimonas* sp. strain SD-212 and amino acid sequence encoded thereby;

SEQ ID NO: 2: amino acid sequence encoded by the crtW gene of *Brevundimonas* sp. strain SD-212;

SEQ ID NO: 3: primer (forward) for amplification of crtW derived from *Brevundimonas* sp. strain SD-212;

SEQ ID NO: 4: primer (reverse) for amplification of crtW derived from *Brevundimonas* sp. strain SD-212;

SEQ ID NO: 5: primer (forward) for amplification of crtW derived from *Paracoccus* sp. strain PC1;

SEQ ID NO: 6: primer (reverse) for amplification of crtW derived from *Paracoccus* sp. strain PC1;

SEQ ID NO: 7: primer (forward) for amplification of crtW derived from *Paracoccus* sp. strain N81106;

SEQ ID NO: 8: primer (reverse) for amplification of crtW derived from *Paracoccus* sp. strain N81106;

SEQ ID NO: 9: nucleotide sequence of the crtZ gene of *Brevundimonas* sp. strain SD-212 and amino acid sequence encoded thereby;

SEQ ID NO: 10: amino acid sequence encoded by the crtZ gene of *Brevundimonas* sp. strain SD-212;

SEQ ID NO: 11: primer (forward) for amplification of crtZ derived from *Brevundimonas* sp. strain SD-212;

SEQ ID NO: 12: primer (reverse) for amplification of crtZ derived from *Brevundimonas* sp. strain SD-212;

SEQ ID NO: 13: primer (forward) for amplification of crtZ derived from *Erwinia uredovora*;

SEQ ID NO: 14: primer (reverse) for amplification of crtZ derived from *Erwinia uredovora*;

SEQ ID NO: 15: primer (forward) for amplification of crtZ derived from *Paracoccus* sp. strain PC1;

SEQ ID NO: 16: primer (reverse) for amplification of crtZ derived from *Paracoccus* sp. strain PC1;

SEQ ID NO: 17: primer (forward) for amplification of crtZ derived from *Paracoccus* sp. strain N81106;

SEQ ID NO: 18: primer (reverse) for amplification of crtZ derived from *Paracoccus* sp. strain N81106;

SEQ ID NO: 19: primer (forward) for amplification of crtZ derived from *Flavobacterium* sp. Strain P99-3; and SEQ ID NO: 20: primer (reverse) for amplification of crtZ derived from *Flavobacterium* sp. Strain P99-3.

Advantageous Effect of the Invention

According to the present invention, a large amount of astaxanthin or metabolites thereof can be prepared by utilizing the crtW gene and/or crtZ gene derived from *Brevundimonas* sp. strain SD-212.

BEST MODE FOR CARRYING OUT THE INVENTION

Figure 1:
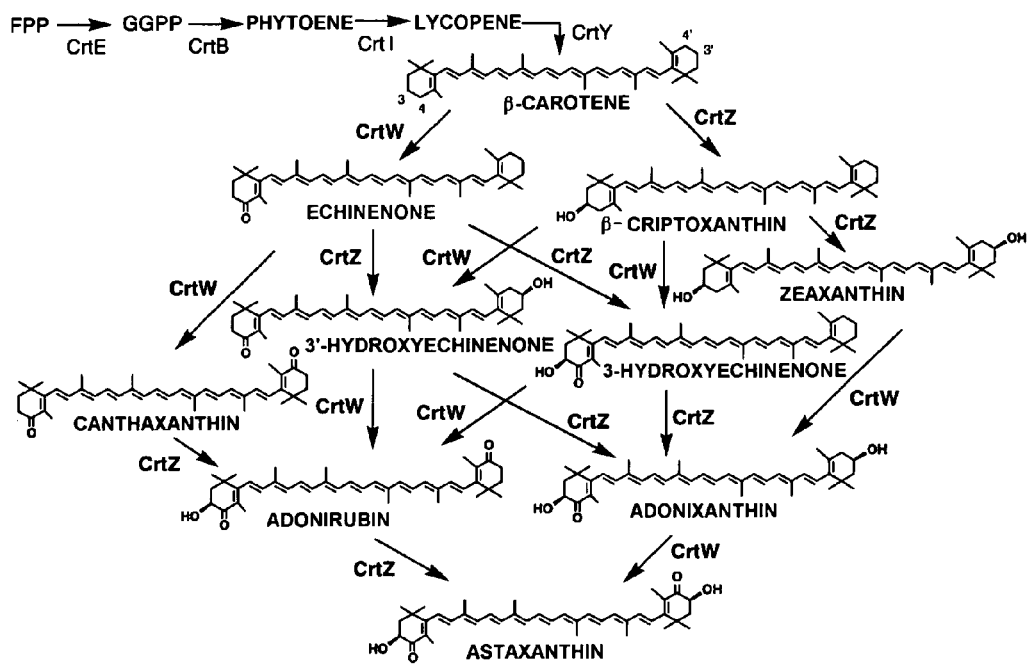
FIG. 1 is a diagram showing astaxanthin biosynthesis pathways and functions of various Crt enzymes in astaxanthin-producing *E. coli*.

The present invention will now be specifically described with reference to Examples. However, the present invention is not limited to these Examples.

EXAMPLES

Example 1

Strains, Plasmids, and Growth Conditions

The strains and plasmids used in the present invention (crtW) are shown in Table 1. The strains were cultured at 37° C. or 30° C. in an LB (Luria-Bertani) medium. When necessary, ampicillin (Ap, 100 μg/ml) or chloramphenicol (Cm, 30 μg/ml) was added to the medium.

TABLE 1

| Strains and Plasmids Used in the Present Invention | | |
|---|---|---|
| Strain/Plasmid | Nature* | Reference/Manufacturer |
| Strain | | |
| *E. coli* JM109 | Host for genetic engineering experiments | Takara |
| JM109Ercrt-zea | *E. coli* strain JM109 with pACCAR25ΔcrtX introduced thereinto | Present invention |

TABLE 1-continued

Strains and Plasmids Used in the Present Invention

| Strain/Plasmid | Nature* | Reference/Manufacturer |
|---|---|---|
| JM109BreW-asta | E. coli strain JM109 with pACCAR25ΔcrtX and pUCBreW introduced thereinto | Present invention |
| JM109ParaPC1W-asta | E. coli strain JM109 with pACCAR25ΔcrtX and pUCParaPC1W introduced thereinto | Present invention |
| JM109ParaN8W-asta | E. coli strain JM109 with pACCAR25ΔcrtX and pUCParaN8W introduced thereinto | Present invention |
| Plasmid | | |
| pACCAR25ΔcrtX | Cm$^r$: plasmid including crtE, crtB, crtI, crtY, and crtZ | Misawa, et al., 1995 |
| pUC18 | Ap$^r$: cloning vector | TOYOBO |
| p5Bre2-15 | Ap$^r$: Brevundimonas sp. strain SD-212 (MBIC03018)-derived 12-kb EcoRI fragment (containing a carotenoid biosynthesis gene cluster) inserted into EcoRI site of pBluescript II KS− | Present invention |
| pPC17 | Ap$^r$: Paracoccus sp. strain PC-1 (MBIC03024)-derived 1.63-kb DNA fragment inserted into PstI and PsEII sites of pBluescript II SK+ | Misawa, et al., 1995 |
| AK96K | Ap$^r$: Paracoccus sp. strain N81106 (MBIC01143)-derived 1.88-kb DNA fragment inserted into BamHI and KpnI sites of pBluescript II SK− | Misawa, et al., 1995 |
| pUCBreW | Ap$^r$: Brevundimonas sp. strain SD-212 (MBIC03018)-derived β-carotene ketolase amplified by PCR and inserted into pUC18 | Present invention |
| pUCParaPC1W | Ap$^r$: Paracoccus sp. strain PC-1 (MBIC03024)-derived β-carotene ketolase amplified by PCR and inserted into pUC18 | Present invention |
| pUCParaN8W | Ap$^r$: Paracoccus sp. strain N81106 (MBIC01143)-derived β-carotene ketolase amplified by PCR and inserted into pUC18 | Present invention |

*Ap$^r$: ampicillin resistance, Cm$^r$: chloramphenicol resistance

Misawa, N., Satomi, Y., Kondo, K., Yokoyama, A., Kajiwara, S., Saito, T., Ohtani, T., and Miki, W., Structure and functional analysis of a marine bacterial carotenoid biosynthesis gene cluster and astaxanthin biosynthetic pathway proposed at the gene level. J. Bacteriol. 177: 6575-6585 1995: Non-Patent Document 1.

Example 2

Genetic Engineering Experiments

Usual genetic engineering experiments such as preparation of plasmids, treatment with restriction enzymes, ligation reaction, and transformation were conducted according to the methods disclosed in Molecular Cloning, Sambrook et al. (1989). Sambrook, J., Fritsch, E. F., and Maniatis T., Molecular cloning: a laboratory manual. 2nd ed. 1989, Cold Spring Harbor Laboratory Press, Cold Spring Harbor, N.Y.

Example 3

Preparation of Chromosomal DNA from Brevundimonas sp. Strain SD-212

Brevundimonas sp. strain SD-212 (SD212; MBIC 03018) was cultured in 300 ml of a Marine Broth (MB) medium (Difco) at 25° C. for 3 days. Cells were harvested, washed with an STE buffer (100 mM NaCl, 10 mM Tris-HCl, 1 mM EDTA, pH 8.0) twice, thermally treated at 68° C. for 15 min, and then suspended in a solution I (50 mM glucose, 25 mM Tris-HCl, 10 mM EDTA, pH 8.0) containing 5 mg/ml lysozyme (Sigma) and 100 µg/ml RNase A (Sigma). After 1 hr incubation at 37° C., Protenase K (Sigma) was added thereto to give a concentration of 250 µg/ml and the resulting mixture was incubated at 37° C. for 10 min. N-Lauroylsarcosin-Na was added thereto to give a final concentration of 1% and mixed gently and thoroughly by inverting. The mixture was incubated at 37° C. for 3 hr. After several times of phenol/chloroform extraction, while slowly adding two volumes of ethanol, chromosomal DNA deposited was wound around a glass rod and rinsed with 70% ethanol. Then, the chromosomal DNA was dissolved in 2 ml of a TE buffer (10 mM Tris-HCl, 1 mM EDTA, pH 8.0) to prepare a chromosomal DNA solution.

Example 4

Amplification of Partial Fragment of Phytoene Desaturase Gene (crtI) by PCR

A partial fragment of a phytoene desaturase gene (crtI) was amplified by PCR using a crtI-Fo primer (5'-TTY GAY GCI GGI CCI ACI GT-3') and a crtI-Re primer (5'-CCI GGR TGI GTI CCI GCI CC-3') and the chromosomal DNA obtained as described above from Brevundimonas sp. strain SD-212 as a template. The primers had been designed utilizing the homology of phytoene desaturase genes (crtI) among carotenoid-producing bacteria. As a thermostable DNA polymerase, La-Taq (TaKaRa) was used. After thermal denaturation at 96° C. for 5 min, 35 cycles of amplification at 98° C. for 20 sec, 58° C. for 30 sec, and 72° C. for 1 min were carried out. The amplified product was confirmed by 1% agarose gel electrophoresis. Then, a 1.1-kb DNA fragment was cut out from the agarose gel and purified (with Qiagen Gel Extraction kit: QIAGEN, or Gene Clean II Kit: BIO101). The purified DNA fragment was ligated to pGEM-T Easy and transformed into E. coli (DH5α). This plasmid was designated pCRTI-SD212. The E. coli was cultured in 2 ml of an LB liquid medium containing ampicillin at 37° C. overnight, and then the plasmid was extracted. The nucleotide sequence (partial) of the extracted plasmid was determined using a Big Dye Terminator Cycle Sequencing Ready Reaction Kit ver.2 (Perkin-Elmer) and a model 3700 DNA sequencer (Perkin-Elmer) according to the attached protocol. The thus determined DNA sequence was subjected to homology search using Blast (Altschul and Lipman, 1990) to confirm that this DNA sequence is a DNA fragment having a homology to the phytoene desaturase gene (crtI). The DNA fragment purified after the PCR was used as a probe in the colony hybridization and Southern hybridization conducted in Examples 6 and 7. Altschul, S. F. and Lipman, D. J., Protein database search for multiple alignments. Proc. Natl. Acad. Sci. USA 87, 5509-5513, 1990.

Example 5

Construction of Cosmid Library

Experimental procedures for obtaining phage particles from a chromosomal DNA solution prepared from *Brevundimonas* sp. strain SD-212 were carried out according to the instructions attached to SuperCos 1 Cosmid Vector Kit available from Stratagene. Briefly, the chromosomal DNA from *Brevundimonas* sp. strain SD-212 was partially digested with Sau3AI and ligated to the BamHI site of a cosmid vector, and was packaged into phage particles using LAMBDA INN (Nippon Gene). Subsequently, *Escherichia coli* strain XL1-Blue MR was infected with the resulting phage particles to obtain about 1000 Ap-resistant colonies on LB plates containing Ap. The resulting colonies were transferred onto fresh LB plates containing an antibiotic with sterilized toothpicks. This cosmid vector SuperCos 1 is a 7.9-kb vector and can carry a DNA fragment of 30 to 45 kb.

Example 6

Colony Hybridization

The colonies (500) from the cosmid library constructed using *E. coli* XL1-Blue MR as the host in Example 5 were screened for clones containing a crtI by colony hybridization using the partial fragment of phytoene desaturase gene (crtI) amplified by the PCR method in Example 4 as a probe. First, the *E. coli* was seeded on plates and cultured at 37° C. At this time, the *E. coli* was seeded at 48 colonies per plate. After overnight culture, a Hybond-N+ membrane (Amersham Pharmacia) having a diameter of 82 mm was placed on each plate and the membrane was marked with an injection needle. The membrane was peeled off and placed (sample side up) on a 3 mm filter paper (Whattman) impregnated with a 10% SDS solution for incubation for 5 min. Then, the DNA on the membrane was incubated for another 5 min on a 3 mm filter paper impregnated with a denaturing solution (1.5 M NaCl, 0.5 M NaOH). Then, the membrane was soaked in a neutralizing solution (1.5 M NaCl, 0.5M Tris-HCl) for 5 min (twice). Further, the membrane was washed with 2×SSC twice. At this time, the membrane was wiped off strongly with Kimtowel so that no cell debris remained on the membrane. After these treatments, the membrane was air-dried on Kimtowel and Kimwipe for 30 min and baked at 80° C. for 2 hr to thereby immobilize DNA on the membrane. A DNA probe was prepared using Alkphos Direct Labeling and Detection System (Amersham Pharmacia) and colony hybridization was conducted according to the attached protocol. As a result, 6 positive clones were obtained from the 500 colonies by the colony hybridization using the partial fragment of phytoene desaturase gene (crtI) as a probe. The plasmids contained in these 6 clones were designated pCos5-1, pCos5-2, pCos7-1, pCos8-1, pCos9-1, and pCos10-1.

Example 7

Southern Hybridization

The 6 positive clones selected in Example 6 were cultured in 2 ml of an LB liquid medium containing Ap at 37° C. overnight, and then plasmid DNA was extracted. The extracted plasmid DNA was completely digested with EcoRI and then subjected to electrophoresis. Then, the DNA was transferred onto a nylon membrane (Hybond N+) by capillary blotting using a 0.4 M NaOH solution. After this treatment, the membrane was baked at 80° C. for 2 hr to thereby immobilize the DNA on the membrane. Then, Southern hybridization was performed using Alkphos Direct Labeling and Detection System (Amersham Pharmacia) according to the attached protocol. The above-described partial fragment of phytoene desaturase gene (crtI) was used as the probe. As a result, positive signals were observed in the 12-kb EcoRI fragment of 3 clones, pCos5-2, pCos7-1, and pCos9-1, out of the 6 positive clones.

Example 8

Analysis of a Carotenoid Gene Cluster

Figure 2:
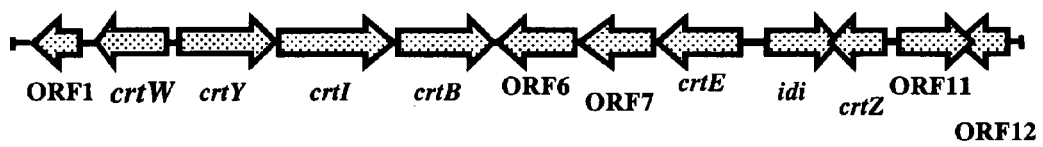
FIG. 2 is a diagram showing the structure of a carotenoid biosynthesis gene cluster of *Brevundimonas* sp. strain SD-212.

The 12-kb insert fragment was cut out from one (pCos5-2) of the positive clones selected in Example 7 with EcoRI, ligated to the EcoRI site of a plasmid vector pBluescript II KS—, and transformed into *E. coli* strain DH5a. This plasmid was designated p5Bre2-15. The resultant *E. coli* was cultured in 2 ml of an LB liquid medium containing Ap at 37° C. overnight, and then the plasmid was extracted. The nucleotide sequence of the extracted plasmid was determined using a Big Dye Terminator Cycle Sequencing Ready Reaction Kit ver.2 (Perkin-Elmer) and a model 3700 DNA sequencer (Perkin-Elmer) according to the attached protocol. Gene-coding regions of the thus determined 11991-bp DNA sequence were estimated using GeneMark.hmm (Lukashin A. and Borodovsky M.) and SD-like sequences were confirmed. As a result, 12 open reading frames (ORFs) were found in the 12-kb fragment (FIG. 2). Each ORF was subjected to homology search at the amino acid sequence level using Blast. Seven ORFs out of twelve ORFs showed homology to existing carotenoid biosynthesis genes (crtW, crtY, crtI, crtB, crtE, crtZ, and idi) (Table 2), and were designated crtW, crtY, crtI, crtB, crtE, crtZ, and idi genes, respectively. The remaining 5 genes were unknown genes having no overall homology to any existing genes.

*Escherichia coli* carrying the plasmid p5Bre2-15 has been deposited at the International Patent Organism Depository, National Institute of Advanced Industrial Science and Technology under the Accession No. P-19580.

TABLE 2

Characteristics and Predicted Functions of the Various ORFs Present in the Carotenoid Biosynthesis Gene Cluster of *Brevundimonas* sp. Strain SD-212

| Designation of ORF | GC % | No. of Amino Acid Residues | Predicted Function | Homology to Gene Product of Other Organism (%) | GeneBank number |
|---|---|---|---|---|---|
| ORF1 | 69.7 | 140 | Unknown | | |
| crtW | 69.6 | 244 | β-carotene C4 oxygenase | CrtW: *Brevundimonas aurantiaca* (96) | AAN86030 |
| crtY | 70.2 | 392 | Lycopene cyclase | CrtY: *Xanthobacter autotrophicus* Py2 (53) | AF408848 |

TABLE 2-continued

Characteristics and Predicted Functions of the Various ORFs Present
in the Carotenoid Biosynthesis Gene Cluster of *Brevundimonas* sp.
Strain SD-212

| Designation of ORF | GC % | No. of Amino Acid Residues | Predicted Function | Homology to Gene Product of Other Organism (%) | GeneBank number |
|---|---|---|---|---|---|
| crtI | 67.5 | 489 | Phytoene desaturase | CrtI: *Xanthobacter autotrophicus* Py2 (72) | AF408848 |
| crtB | 72 | 310 | Phytoene synthase | CrtB: *Xanthobacter autotrophicus* Py2 (54) | AF408848 |
| ORF6 | 75.8 | 355 | Unknown | | |
| ORF7 | 74.6 | 315 | Unknown | | |
| crtE | 71 | 298 | GGPP synthase | CrtE: *Xanthobacter autotrophicus* Py2 (42) | AF408847 |
| idi | 74.9 | 350 | Type II IPP isomerase | IPP isomerase: *Pantoea agglomerans* Eho10 (55) | Q01335 |
| crtZ | 66.9 | 161 | β-carotene C3 hydroxylase | CrtZ: *Alcaligenes* sp. PC1 (49) | Q44262 |
| ORF11 | 70.7 | 257 | Unknown | | |
| ORF12 | 66.7 | 122 | Unknown | | |

CrtW, *Brevundimonas aurantiaca* (GeneBank No. AAN86030);
CrtY, CrtI, CrtB, CrtE, *Xanthobacter* sp. Py2 (GeneBank No. AF408848, AF408847);
IPP isomerase, *Pantoea agglomerans* Eho10 (*Erwinia herbicola*) (GeneBank No. Q01335);
CrtZ, *Alcaligenes* sp. PC1 (GeneBank No. Q44262)

Lukashin A. and Borodovsky M., GeneMark.hmm: new solutions for gene finding, NAR, Vol. 26, No. 4, pp. 1107-1115, 1998.

Misawa, N., Nakagawa, M., Kobayashi, K., Yamano, S., Izawa, Y., Nakamura, K. and Harashima, K., Elucidation of the *Erwinia uredovora* carotenoid biosynthetic pathway by functional analysis of gene products expressed in *Escherichia coli*, J. Bacteriol. 172, 6704-6712, 1990.

Misawa, N., Satomi, Y., Kondo, K., Yokoyama, A., Kajiwara, S., Saito, T., Ohtani, T., and Miki, W., Structure and functional analysis of a marine bacterial carotenoid biosynthesis gene cluster and astaxanthin biosynthetic pathway proposed at the gene level, J. Bacteriol. 177, 6575-6585, 1995 (Non-Patent Document 1).

Hannibal, L., Lorquin, J., D'Ortoli, N. A., Garcia, N., Chaintreuil, C., Masson-Boivin, C., Dreyfus, B. and Giraud, E., Isolation and characterization of canthaxanthin biosynthesis genes from the photosynthetic bacterium *Bradyrhizobium* sp. strain ORS278, J. Bacteriol. 182, 3850-3853, 2000.

Larsen, R. A., Wilson, M. M., Guss, A. M. and Metcalf, W. W., Genetic analysis of pigment biosynthesis in Xanthobacter autotrophicus Py2 using a new, highly efficient transposon mutagenesis system that is functional in a wide variety of bacteria, Arch. Microbiol. 178, 193-201, 2002.

The enzyme CrtW encoded by the crtW gene of *Brevundimonas* sp. Strain SD-212 is a peptide consisting of 244 amino acids. The amino acid sequence is shown in SEQ ID NO: 2, and the nucleotide sequence of the crtW gene and the deduced amino acid sequence are shown in SEQ ID NO: 1. The CrtW from *Brevundimonas* sp. Strain SD-212 has a homology (identity) of only 46% to both the CrtW of *Paracoccus* sp. Strain N81106 (DDBJ/Genbank accession No. D58420) and the CrtW of *Paracoccus* sp. Strain PC-1 (DDBJ/Genbank accession No. D58422) at the amino acid sequence level. As shown in Table 2, the CrtW from *Brevundimonas* sp. Strain SD-212 has a homology (identity) of 96% to the CrtW from *Brevundimonas aurantiaca*, but the CrtW of *Brevundimonas aurantiaca* about which nothing is known other than the sequence that is merely disclosed on the net. Thus, functions and characteristics of this enzyme are not known at all.

Example 9

Construction of β-Galactosidase Fusion Protein Expression Plasmids

The individual crtW genes were amplified by PCR and the individual plasmids for expressing each β-galactosidase fusion protein were constructed so as to synthesize each crtW gene product fused to a lead sequence of β-galactosidase gene (lacZ) by an *E. coli* vector pUC18 (TOYOBO). Specifically, required DNA fragments were amplified by PCR using p5Bre2-15, pPC17, or pAK96K as a DNA template and primers (shown in SEQ ID NOS: 3 to 8) designed so that each amplified crtW product having an EcoRI site at the 5'-end and a BamHI site at the 3'-end could be obtained. The pPC17 and pAK96K are plasmids containing the crtW genes derived from *Paracoccus* sp. strain PC-1 and *Paracoccus* sp. N81106, respectively.

PfuTurbo Hotstart DNA Polymerase (Stratagene) was used as a thermostable DNA polymerase. After thermal denaturation at 95° C. for 20 sec, 30 cycles of amplification at 95° C. for 20 sec, 51° C. for 30 sec, and 72° C. for 1 min and 30 sec were carried out. A part of the amplified product was confirmed by 1% agarose gel electrophoresis. The remaining amplified product was precipitated with ethanol, digested with EcoRI and BamHI, and then was subjected to 1% agarose gel electrophoresis. Then, the DNA fragment with an expected length was cut out from the agarose gel and purified (using a Gene Clean Turbo Kit: Q-BIOgene). The purified DNA was ligated to the EcoRI and BamHI sites of pUC18 and transformed into *E. coli* JM109. The lead sequence in these β-galactosidase fusion protein expression plasmids, with the seven amino acid residues Met-Thr-Met-Ile-Thr-Asn-Ser, was designed to be added to the Met of the original start of the individual crtW.

Example 10

Construction of Zeaxanthin- or Astaxanthin-Producing *E. Coli*

The *E. coli* clones carrying the plasmid containing the individual crtW genes were each cultured in 4 ml of an LB liquid medium containing Ap at 37° C. overnight, and then the plasmid was extracted. The nucleotide sequence of the extracted plasmid was confirmed using a Big Dye Terminator Cycle Sequencing Ready Reaction Kit ver.2 (Perkin-Elmer) and a model 3700 DNA sequencer (Perkin-Elmer) according to the attached protocol. The individual plasmids which were confirmed to contain the correct nucleotide sequence of crtW gene derived from *Brevundimonas* sp. strain SD-212, *Paracoccus* sp. strain PC-1, or *Paracoccus* sp. strain N81106 were designated pUCBreW (lacZ::crtW), pUCParaPC1W (lacZ::

crtW), and pUCParaN8W (lacZ::crtW), respectively. Zeaxanthin-producing E. coli was constructed by introducing a plasmid pACCAR25ΔcrtX into E. coli JM109 and selecting Cm-resistant colonies. Further, astaxanthin-producing E. coli was constructed by introducing a plasmid pACCAR25ΔcrtX with pUCBreW, pUCParaPC1W, or pUCParaN8W into E. coli and selecting Ap- and Cm-resistant colonies. The E. coli clones were designated JM109Ercrt-zea, JM109BreW-asta, JM109ParaPC1W-asta, and JM109ParaN8W-asta.

Example 11

Analysis of Astaxanthin-Producing Efficiency in E. Coli Expressing Individual crtW Genes JM109Ercrt-zea was cultured in 4 ml of an LB liquid medium containing Cm and JM109BreW-asta, JM109ParaPC1W-asta, and JM109ParaN8W-asta were each cultured in 4 ml of an LB liquid medium containing Ap and Cm, at 37° C. overnight. Fifty microliters of each of the LB liquid media were inoculated into 4 ml of an LB liquid medium and subjected to main culture at 30° C. When $A_{600}$ became about 0.5, 0.5 mM of IPTG (isopropyl-β-D-thiogalactopyranoside) was added to the culture medium, followed by further culturing at 30° C. The cells were harvested by centrifuging the culture medium and washed with STE twice. Acetone (400 μl) was added thereto and vortexed to thereby transfer pigments from cells to acetone. The resulting mixture was centrifuged. The supernatant was filtered and subjected to pigment analysis with an HPLC-PDA system (Waters Alliance 2695 and 2996 photodiode array detector) or an HPLC-PDA-MS system (Shiseido Nano Space SI-2 and ThermoQuest LCQ advantage). In the HPLC-PDA, a TSK gel ODS-80Ts column (TOSOH) was used. The mobile phases were solution A (95% methanol) and solution B [methanol : tetrahydrofuran (THF)=7:3]. The elution program with a flow rate of 1.0 ml/min was as follows: 100% of the solution A for 5 min, a linear gradient from 100% of the solution A to 100% of the solution B for 5 to 10 min, and the solution B for 8 min. Pigments were detected with a photodiode array detector and analyzed with an accessory software Empower. In the HPLC-PDA-MS, a Deverosil C30-UG-3 (1.0 mm i.d.×150 mm) column (Nomura Chemical) was used, and Devorosil C30-UG-S was used as a pre-column. The mobile phases were solution A (95% methanol) and solution B [methanol : tert-butylmethylether (tBME)=3:7]. The elution program with a flow rate of 0.09 ml/min was as follows: 100% of the solution A for 15 min, a linear gradient from 100% of the solution A to 100% of the solution B for 15 to 115 min, and the solution B for 20 min.

Figure 3:
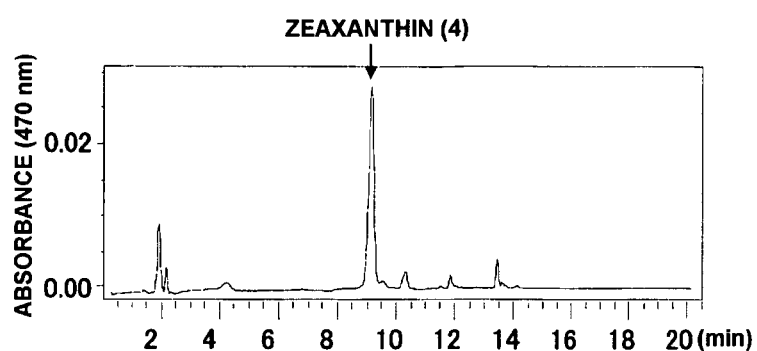
FIG. 3 is graphs showing the results of HPLC-PDA analysis of pigments accumulated in various recombinant *E. coli* cells (cultured for 48 hr after the addition of IPTG). (In the graphs, peaks indicated by reference numeral 1 are for astaxanthin, peaks indicated by reference numeral 2 are for adonixanthin, peaks indicated by reference numeral 3 are for adonirubin, a peak indicated by reference numeral 4 is for zeaxanthin, peaks indicated by reference numeral 5 are for 3'-hydroxyechinenone, peaks indicated by reference numeral 6 are for 3-hydroxyechinenone, and peaks indicated by reference numeral 7 are for lycopene.) a) HPLC chromatogram (470 nm) of pigments produced by JM109Ercrt-zea, b) HPLC chromatogram (470 nm) of pigments produced by JM109BreW-asta, c) HPLC chromatogram (470 nm) of pigments produced by JM109ParaPC1W-asta, and d) HPLC chromatogram (470 nm) of pigments produced by JM109ParaN8W-asta.
Figure 3:
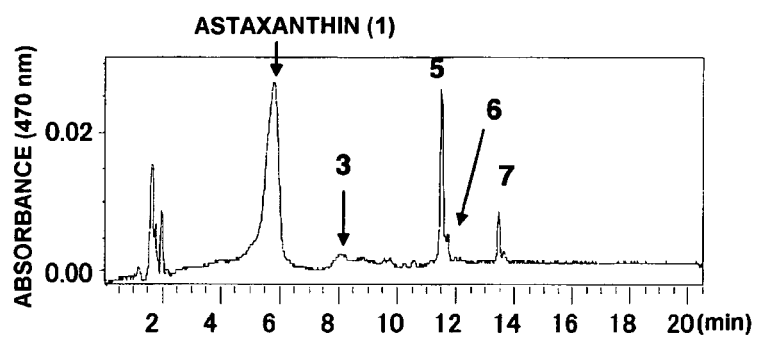
Figure 3:
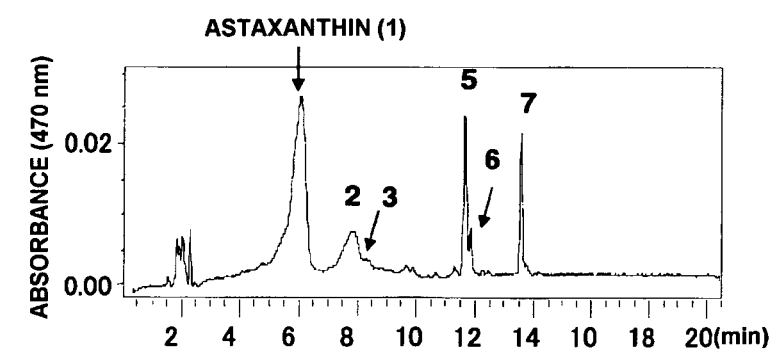
Figure 3:
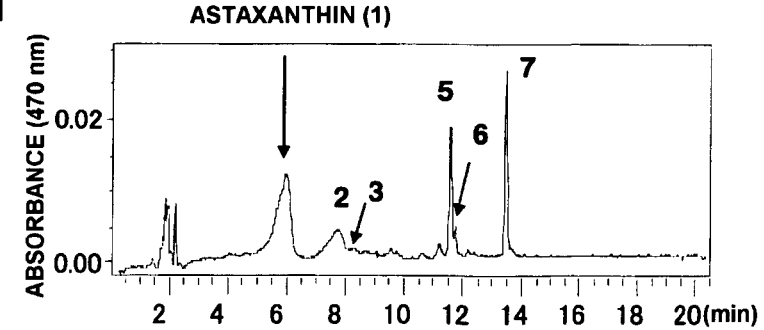
Figure 4:
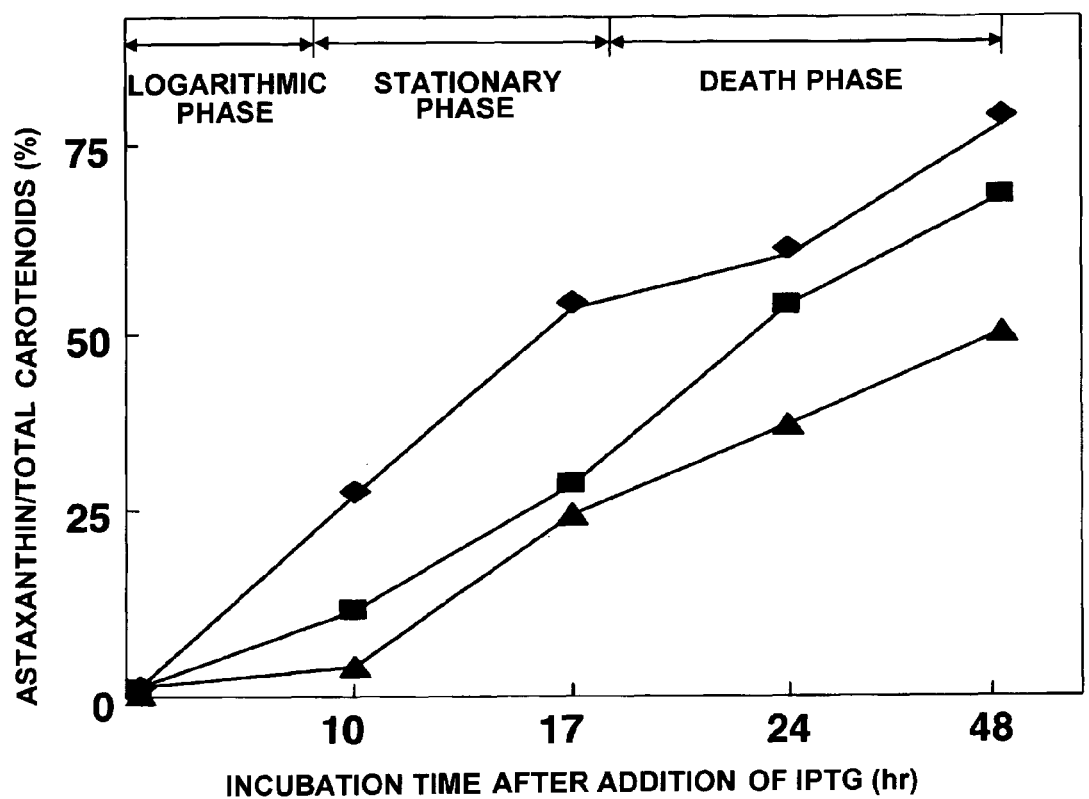
FIG. 4 is a graph showing the relationship between incubation times and the amounts of astaxanthin accumulated in various recombinant *E. coli* cells.

Analysis of pigments produced by the various E. coli clones was conducted 48 hr after the addition of IPTG using an HPLC-PDA system and HPLC-PDA-MS system (see FIG. 3). The results shows that almost all of pigments produced by JM109Ercrt-zea were zeaxanthin (HPLC/PDA: RT 8.5 min, λmax 450, 479 nm; HPLC/PDA/MS: RT 25.55 min, λmax 450, 476 nm, m/z 569.2 [M+H]$^+$) (see FIG. 3a). In JM109BreW-asta, in addition to a peak of the main pigment, astaxanthin, (HPLC/PDA: RT 5.8 min, λmax 473 nm; HPLC/PDA/MS: RT 13.28, λmax 476 nm, m/z 597.2 [M+H]$^{3o}$), peaks of adonirubin (Poenicoxanthin) (HPLC/PDA: RT 8.1 min; HPLC/PDA/MS: RT 20.92 min, λmax 469 nm, m/z 581.2 [M+H]$^+$), 3'-hydroxyechinenone (HPLC/PDA: RT 11.5 min, λmax 473; HPLC/PDA/MS: RT 62.10 min, λmax 469, m/z 567.2 [M+H]$^+$), 3-hydroxyechinenone (HPLC/PDA: RT 11.7 min; HPLC/PDA/MS: RT 62.72 min, m/z 567.2 [M+H]$^+$), and lycopene (HPLC/PDA: RT 13.4 min, λmax 446, 473, 505 nm; HPLC/PDA/MS: RT 90.27 min, λmax 444, 471, 501 nm, m/z 537.1) were observed (FIG. 3b). In JM109ParaPC1W-asta and JM109ParaN8W-asta, in addition to peaks of the above-mentioned carotenoids, a peak of adonixanthin (HPLC/PDA: RT 7.6 min; HPLC/PDA/MS: RT 17.45 min, λmax 460, 482 nm, m/z 583.2 [M+H]$^+$) was observed (FIGS. 3c and d). The astaxanthin contents in the carotenoids accumulated in JM109BreW-asta, JM109ParaPC1W-asta, and JM109ParaN8W-asta were 75%, 65%, and 47%, respectively. Thus, the astaxanthin content in JM109BreW-asta was the highest (FIG. 3). Furthermore, 3'-hydroxyechinenone was apt to accumulate in every pigment extract from recombinant E. coli clones, JM109BreW-asta, JM109ParaPC1W-asta, and JM109ParaN8W-asta, and any difference in the amount was not observed among the recombinant E. coli clones. On the other hand, in the pigment extract of JM109BreW-asta, no peak of adonixanthin, which was observed in the pigment extracts of JM109ParaPC1W-asta and JM109ParaN8W-asta, was observed. Therefore, it is predicted that JM109BreW-asta has a high conversion efficiency of adonixanthin into astaxanthin and, as a result, has a high production efficiency of astaxanthin. Further, in order to confirm this, the relationship between incubation time and production efficiency of astaxanthin. Escherichia coli was collected 10, 17, and 24 hr after the addition of IPTG, and the amounts of accumulated pigments were analyzed (FIG. 4). The astaxanthin biosynthesis efficiency of JM109BreW-asta (symbol in the figure: ◆) was significantly high compared to those of JM109ParaPC1W-asta (symbol in the figure: ■) and JM109ParaN8W-asta (symbol in the figure: ▲) by the stationary phase, and then the difference in the efficiency was gradually decreased in the death phase.

Figure 5:
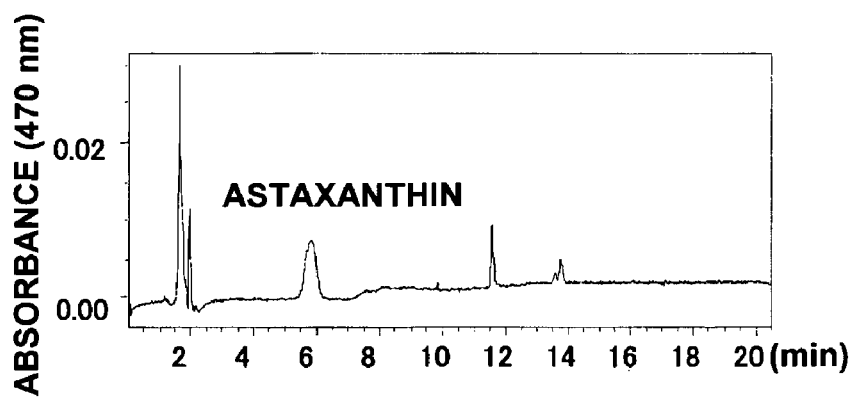
FIG. 5 is graphs showing the results of HPLC-PDA analysis of pigments accumulated in various recombinant *E. coli* cells (cultured for 6 hr after the addition of IPTG). a) HPLC chromatogram (470 nm) of pigments produced by JM109BreW-asta, b) HPLC chromatogram (470 nm) of pigments produced by JM109ParaPC1W-asta, and c) HPLC chromatogram (470 nm) of pigments produced by JM109ParaN8W-asta.
Figure 5:
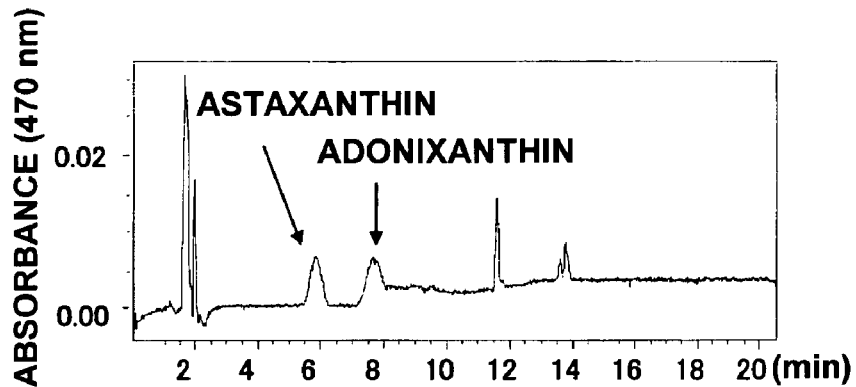
Figure 5:
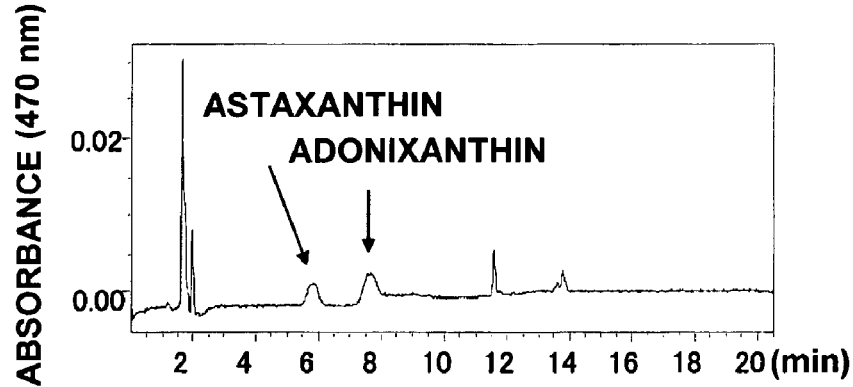

Further, the tendency in which adonixanthin was accumulated in JM109ParaPC1W-asta and JM109ParaN8W-asta but not in JM109BreW-asta was observed during all culture phases. In particular, in the pigment analysis 6 hr after the addition of IPTG, a large amount of adonixanthin (similar amount of astaxanthin) was accumulated in JM109ParaPC1W-asta and JM109ParaN8W-asta (FIGS. 5b and c). However, in JM109BreW-asta, adonixanthin was not accumulated at all and the production amount of astaxanthin was increased instead (FIG. 5a).

As a result of this study, it has been revealed that CrtW derived from Brevundimonas sp. strain SD-212 has a high efficiency of converting adonixanthin into astaxanthin and most effectively produces astaxanthin. These results show that the crtW gene derived from Brevundimonas sp. strain SD-212 is effective for mass-production for industrial use of astaxanthin and metabolites thereof (astaxanthin ester and the like) using a recombinant microorganism or recombinant plant.

Example 12

Strains, Plasmids, and Growth Conditions

The strains and plasmids used in the present invention (crtZ) are shown in Table 3. The strains were cultured at 37° C. or 30° C. in an LB (Luria-Bertani) medium. When necessary, ampicillin (Ap, 100 μg/ml) or chloramphenicol (Cm, 30 μg/ml) was added to the medium.

TABLE 3

Strains and Plasmids used in the Present invention

| Strain/Plasmid | Nature* | Reference/Manufacturer |
|---|---|---|
| Strain | | |
| E. coli JM109 | Host for genetic engineering experiments | Takara |
| JM109Pancrt-Cantha | E. coli strain JM109 with pAC-Cantha introduced thereinto | Present invention |
| JM109BreZ-asta | E. coli strain JM109 with pAC-Cantha and pUCBreZ introduced thereinto | Present invention |
| JM109PanZ-asta | E. coli strain JM109 with pAC-Cantha and pUCpanZ introduced thereinto | Present invention |
| JM109ParaPC1Z-asta | E. coli strain JM109 with pAC-Cantha and pUCParaPC1Z introduced thereinto | Present invention |
| JM109ParaN8Z-asta | E. coli strain JM109 with pAC-Cantha and pUCParaN8Z introduced thereinto | Present invention |
| JM109P99Z-asta | E. coli strain JM109 with pAC-Cantha and pUCP99Z introduced thereinto | Present invention |
| Plasmid | | |
| pAC-Cantha | $Cm^r$: plasmid including crtE, crtB, crtI, crtY, and crtW | Nishida, et al., unpublished data |
| pUC18 | $Ap^r$: cloning vector | TOYOBO |
| pUC8 | $Ap^r$: cloning vector | TOYOBO |
| p5Bre2-15 | $Ap^r$: Brevundimonas sp. strain SD-212 (MBIC03018)-derived 12-kb DNA fragment inserted into EcoRI site of pBluescript II KS– | Present invention |
| pCAR25 | $Ap^r$: Pantoea ananatis sp. strain 20D3 (D90087)-derived 6.9-kb DNA fragment inserted into KpnI and HindIII sites of pUC19 | Misawa, et al., 1990 |
| pPC17 | $Ap^r$: Paracoccus sp. strain PC-1 (MBIC03024)-derived 1.63-kb DNA fragment inserted into PstI and PstEII sites of pBluescript II SK+ | Misawa, et al., 1995 |
| AK96K | $Ap^r$: Paracoccus sp. strain N81106 (MBIC01143)-derived 1.88-kb DNA fragment inserted into BamHI and KpnI sites of pBluescript II SK– | Misawa, et al., 1995 |
| pBS606 | $Ap^r$: Flavobacteria sp. strain P99-3 (AB106143)-derived 8.9-kb DNA fragment inserted into BglIII and SalI sites of pBluescript II SK– | Teramoto, et al., 2003 |
| pUCBreZ | $Ap^r$: Brevundimonas sp. strain SD-212 (MBIC03018)-derived β-carotene hydroxylase amplified by PCR and inserted into pUC18 | Present invention |
| pUCPanZ | $Ap^r$: Pantoea ananatis sp. strain 20D3 (D90087)-derived β-carotene hydroxylase amplified by PCR and inserted into pUC18 | Present invention |
| pUCParaPC1Z | $Ap^r$: Paracoccus sp. strain PC-1 (MBIC03024)-derived β-carotene hydroxylase amplified by PCR and inserted into pUC18 | Present invention |
| pUCParaN8Z | $Ap^r$: Paracoccus sp. strain N81106 (MBIC01143)-derived β-carotene hydroxylase amplified by PCR and inserted into pUC18 | Present invention |
| pUCP99Z | $Ap^r$: Flavobacteria sp. strain P99-3 (AB106143)-derived β-carotene hydroxylase amplified by PCR and inserted into pUC8 | Present invention |

*$Ap^r$: ampicillin resistance, $Cm^r$: chloramphenicol resistance

Misawa, N., Nakagawa, M., Kobayashi, K., Yamano, S., Izawa, Y., Nakamura, K., and Harashima, K., Elucidation of the *Erwinia uredovora* carotenoid biosynthetic pathway by functional analysis of gene products expressed in *Escherichia coli*, J. Bacteriol. 172: 6704-6712, 1990.

Misawa, N., Satomi, Y., Kondo, K., Yokoyama, A., Kajiwara, S., Saito, T., Ohtani, T., and Miki, W., Structure and functional analysis of a marine bacterial carotenoid biosynthesis gene cluster and astaxanthin biosynthetic pathway proposed at the gene level, J. Bacteriol. 177: 6575-6585, 1995: Non-Patent Document 1.

Teramoto, M., Takaichi, S., Inomata, Y., Ikenaga, H., and Misawa, N., Structural and functional analysis of a lycopene β-monocyclase gene isolated from a unique marine bacterium that produces myxol, FEBS Lett. 545: 120-126, 2003.

Example 13

Construction of β-Galactosidase Fusion Protein Expression Plasmids

The individual crtZ genes were each amplified by PCR and the individual plasmids for expressing each β-galactosidase fusion protein were constructed so as to synthesize each crtZ gene product fused to a lead sequence of β-galactosidase gene (LacZ) by an *E. coli* vector pUC18 or pUC8 (TOYOBO). Specifically, required DNA fragments were amplified by PCR using plasmids p5Bre2-15, pCAR25, pPC17, pAK96K, and pBS606 as DNA templates and primers (shown in SEQ ID NOS: 11 to 20) designed in such a manner that each crtZ amplified product having an EcoRI site at the 5'-end and a BamHI site at the 3'-end (p5Bre2-15, pCAR25, pPC17, and pAK96K) or having an SmaI site at the 5'-end and a HindIII site at the 3'-end (pBS606) could be obtained. The pCAR25, pPC17, pAK96K, and pBS606 were plasmids containing crtZ genes derived from *Pantoea ananatis* strain 20D3 (former name: *Erwinia uredovora*), *Paracoccus* sp. strain PC-1, *Paracoccus* sp. strain N81106, and *Flavobacterium* sp. strain P99-3, respectively.

PfuTurbo Hotstart DNA Polymerase (Stratagene) was used as a thermostable DNA polymerase. After thermal denaturation at 95° C. for 20 sec, 30 cycles of amplification at 95° C. for 20 sec, 51° C. for 30 sec, and 72° C. for 1 min and 30 sec were carried out. A part of the amplified product was confirmed by 1% agarose gel electrophoresis. The remaining amplified product was precipitated with ethanol, digested with EcoRI and BamHI (when p5Bre2-15, pCAR25, pPC17, or pAK96K was used as the template) or with SmaI and HindIII (when pBS606 was used as the template), and then was subjected to 1% agarose gel electrophoresis. Then, the DNA fragment with an expected length was cut out from the agarose gel and purified (using a Gene Clean Turbo Kit: Q-BIOgene). The purified DNA was ligated to the EcoRI and BamHI sites of pUC18 or the SmaI and HindIII sites of pUC8 and transformed into *E. coli* JM109. The lead sequence in these β-galactosidase fusion protein expression plasmids, with 7 or 9 amino acids, i.e., Met-Thr-Met-Ile-Thr-Asn-Ser (when p5Bre2-15, pCAR25, pPC17, or pAK96K was used as the template) or Met-Thr-Met-Ile-Thr-Asn-Ser-Arg-Gly (when pBS606 was used as the template), was designed to be added to the Met of the original start of the individual crtZ.

Example 14

Construction of Canthaxanthin- or Astaxanthin-Producing *E. Coli*

The *E. coli* clones carrying the plasmid containing the individual ertZ genes were each cultured in 4 ml of an LB liquid medium containing Ap at 37° C. overnight, and then the plasmid was extracted. The nucleotide sequence of the extracted plasmid was confirmed using a Big Dye Terminator Cycle Sequencing Ready Reaction Kit ver.2 (Perkin-Elmer) and a model 3700 DNA sequencer (Perkin-Elmer) according to the attached protocol. The individual plasmids which were confirmed to contain the correct nucleotide sequence of crtZ gene derived from *Brevundimonas* sp. strain SD-212, *Pantoea ananatis* strain 20D3, *Paracoccus* sp. strain PC1, *Paracoccus* sp. strain N81106, or *Flavobacterium* sp. stain P99-3 were designated pUCBreZ, pUCPanZ, pUCParaPC1Z, pUCParaN8Z, and pUCP99Z, respectively. Canthaxanthin-producing *E. coli* (referred to as JM109Pancrt-Cantha) was constructed by introducing a plasmid pAC-Cantha into *E. coli* JM109 and selecting Cm-resistant colonies. Further, astaxanthin-producing *E. coli* was constructed by introducing a plasmid pAC-Cantha with pUCBreZ, pUCPanZ, pUCParaPC1Z, pUCParaN8W, or pUCP99Z into *E. coli* and selecting Ap- and Cm-resistant colonies. The *E. coli* transformants were designated JM109BreZ-asta, JM109PanZ-asta, JM109ParaPC1Z-asta, JM109ParaN8Z-asta, and JM109P99Z-asta.

Example 15

Analysis of Astaxanthin-Producing Efficiency in *E. Coli* Expressing Individual crtZ Genes JM109Pancrt-Cantha was cultured in 4 ml of an LB liquid medium containing Cm and JM109BreZ-asta, JM109PanZ-asta, JM109ParaPC1Z-asta, JM109ParaN8Z-asta, and JM109P99Z-asta were each cultured in 4 ml of an LB liquid medium containing Ap and Cm at 37° C. overnight. Fifty microliters of each of the LB liquid media were inoculated into 4 ml of an LB liquid medium and subjected to main culture at 30° C. When $A_{600}$ became about 0.5, 0.5 mM of IPTG (isopropyl-β-D-thiogalactopyranoside) was added to the culture medium, followed by further culturing at 30° C. The cells were harvested by centrifugation of the culturing medium and washed with STE twice. Acetone (400 µl) was added thereto and vortexed to thereby transfer pigments from cells to acetone. The resulting mixture was centrifuged. The supernatant was filtered and subjected to pigment analysis with an HPLC-PDA system (Waters Alliance 2695 and 2996 photodiode array detector). In the HPLC-PDA, a TSK gel ODS-80Ts column (TOSOH) was used. The mobile phases were solution A (95% methanol) and solution B [methanol : tetrahydrofuran (THF)=7:3]. The elution program with a flow rate of 1.0 ml/min was as follows: 100% of the solution A for 5 min, a linear gradient from 100% of the solution A to 100% of the solution B for 5 to 10 min, and the solution B for 8 min. Pigments were detected with a photodiode array detector and analyzed with an accessory software Empower.

Figure 6:
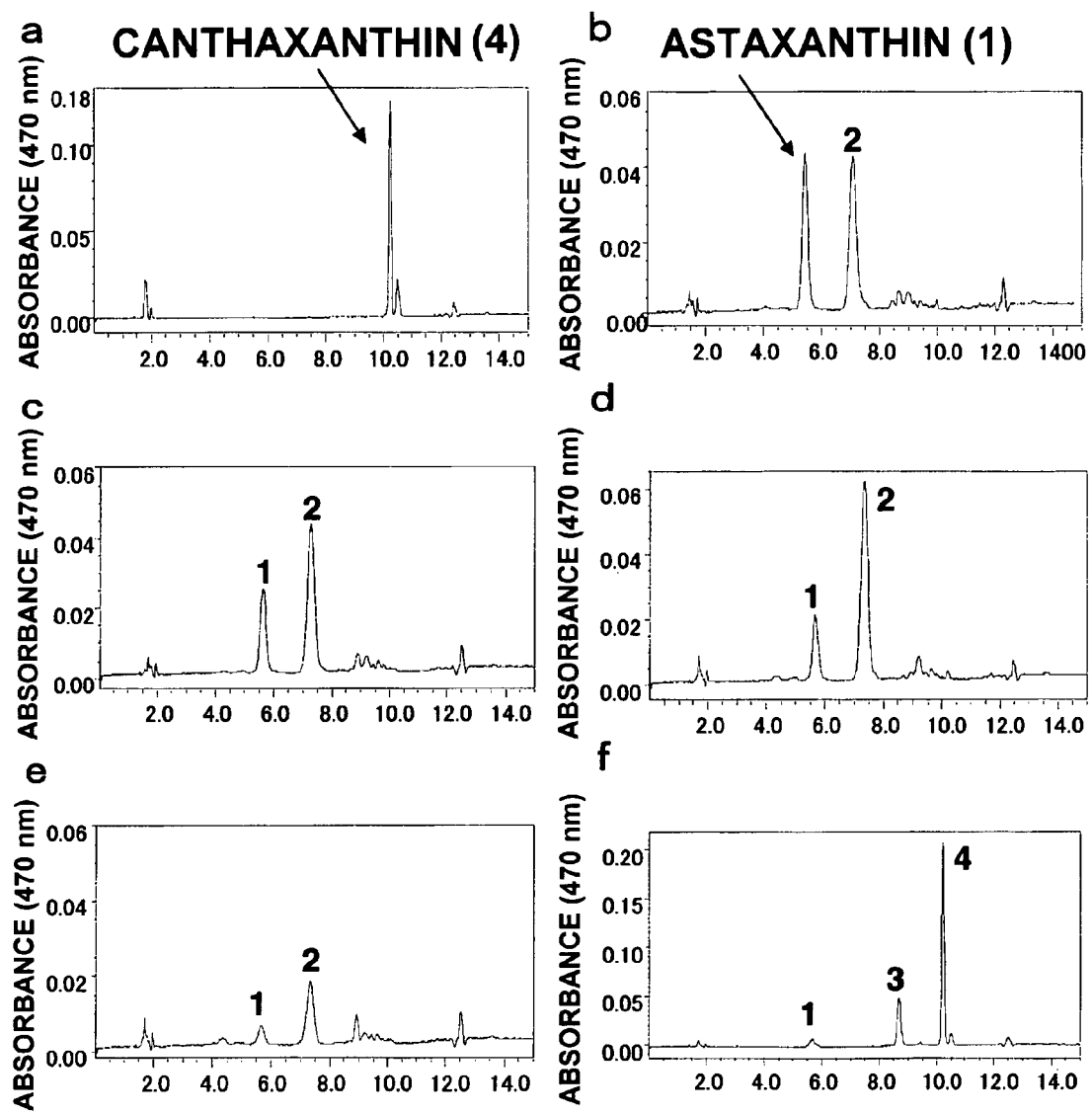
FIG. 6 is graphs showing the results of HPLC-PDA analysis of pigments accumulated in various recombinant *E. coli* cells (cultured for 48 hr after the addition of IPTG). (In the graphs, peaks indicated by reference numeral 1 are for astaxanthin, peaks indicated by reference numeral 2 are for adonixanthin, a peaks indicated by reference numeral 3 is for adonirubin, and peaks indicated by reference numeral 4 are for canthaxanthin.) a) HPLC chromatogram (470 nm) of pigments produced by JM109Pancrt-Cantha, b) HPLC chromatogram (470 nm) of pigments produced by JM109BreZ-asta, c) HPLC chromatogram (470 nm) of pigments produced by JM109PanZ-asta, d) HPLC chromatogram (470 nm) of pigments produced by JM109ParaPC1Z-asta, e) HPLC chromatogram (470 nm) of pigments produced by JM209ParaN8Z-asta, and f) HPLC chromatogram (470 nm) of pigments produced by JM109P99Z-asta.
Figure 7:
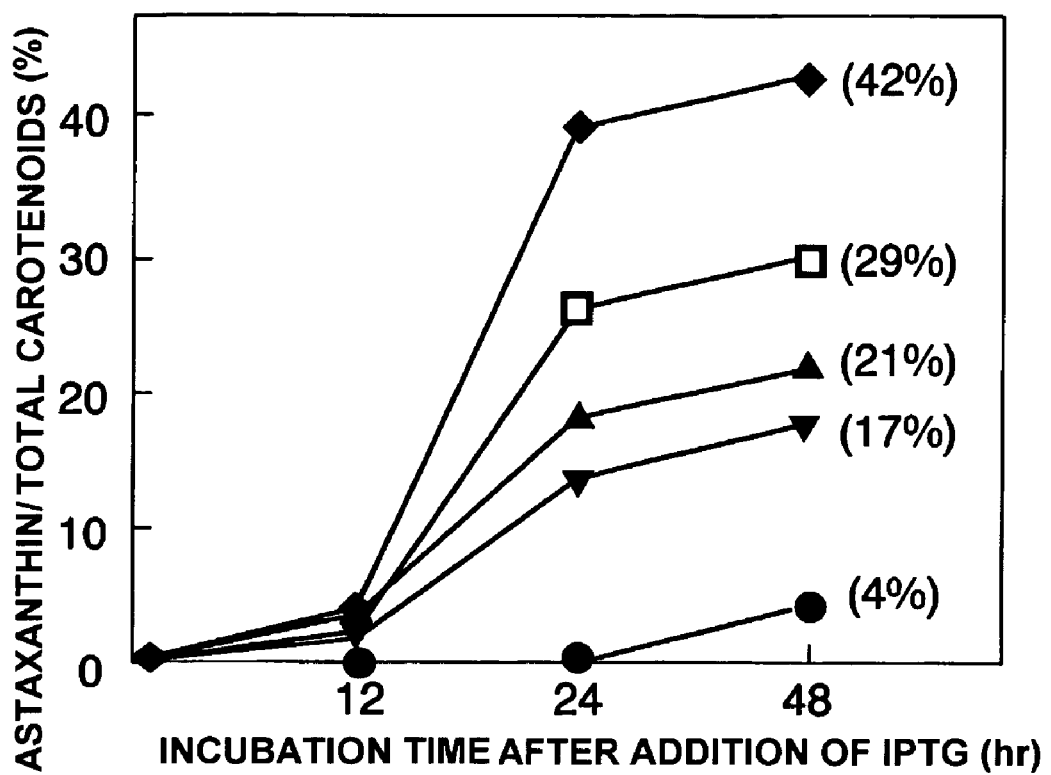
FIG. 7 is a graph showing the relationship between incubation times and the amounts of astaxanthin accumulated in various recombinant *E. coli* cells.

Analysis of pigments produced by various *E. coli* clones was conducted 48 hr after the addition of IPTG using an HPLC-PDA system (see FIG. 6). The results shows that almost all of pigments produced by JM109Pancrt-Cantha were canthaxanthin (RT 10.2 min, λmax 478 nm) (see FIG. 6a). In each of JM109BreZ-asta, JM109PanZ-asta, JM109ParaPC1Z-asta, and JM109ParaN8Z-asta, in addition to a peak of the main pigment, astaxanthin, (RT 5.7 min, λmax 476 nm), a peak of adonixanthin (RT 7.2 min, λmax 463 nm) was observed (FIGS. 6b, c, d, and e). In JM109P99Z-asta, canthaxanthin and adonirubin (Poenicoxanthin) (RT 8.6 min, λmax 470) were main pigments (FIG. 6f). Further, as shown in FIG. 7, the astaxanthin contents in carotenoids accumulated in JM109BreZ-asta (symbol in the figure: ◆), JM109PanZ-asta (symbol in the figure: ☐), JM109ParaPC1Z-asta (symbol in the figure: ▲), JM109ParaN8Z-asta (symbol in the figure: ▼), and JM109P99Z (symbol in the figure: ●) after 48 hr after addition of IPTG were 42%, 29%, 21%, 17%, and 4%, respectively, and the content in JM109BreZ-asta was the highest during all culture phases.

As a result of this study, it has been revealed that CrtZ derived from *Brevundimonas* sp. strain SD-212 most effectively produces astaxanthin. These results show that the crtZ gene derived from *Brevundimonas* sp. strain SD-212 is effective for mass-production for industrial use of astaxanthin and metabolites thereof (astaxanthin ester and the like) using a recombinant microorganism or recombinant plant.

The present specification encompasses the contents disclosed in the specifications and/or drawings of Japanese Patent Applications No. 2004-166625 based on which the present patent application claims priority. All publications, patents, and patent applications cited herein are incorporated herein by reference in their entirety.

The invention claimed is:

1. A microorganism or a plant transformed with a β-ionone ring-4-ketolase gene encoding (a) a peptide comprising the amino acid sequence set forth in SEQ ID NO: 2 and having a β-ionone ring-4-ketolase activity; or (b) a peptide comprising an amino acid sequence derived from the amino acid sequence set forth in SEQ ID NO: 2 by addition, deletion, or substitution of five or fewer amino acids and having a β-ionone ring-4-ketolase activity, the microorganism or the plant being capable of synthesizing astaxanthin or an ester of astaxanthin.

2. The microorganism or the plant according to claim 1, wherein the microorganism or the plant is transformed by introducing said β-ionone ring-4-ketolase gene with at least one other carotenoid biosynthesis gene thereinto.

3. The microorganism or the plant according to claim 2, wherein the at least one other carotenoid biosynthesis gene is all or a part of a gene cluster required for synthesizing a carotenoid containing a β-ionone ring that is hydroxylated at the position 3, from farnesyl pyrophosphate.

4. The microorganism according to claim 1, wherein the microorganism is *Escherichia coli*.

5. A method for preparing astaxanthin or an ester of astaxanthin, which comprises culturing the microorganism according to claim 1 in a medium and obtaining astaxanthin or an ester of astaxanthin from the culture or cells.

6. A method for preparing astaxanthin or a metabolite thereof, which comprises cultivating the plant according to claim 1 and obtaining astaxanthin or an ester of astaxanthin from the plant.

7. The microorganism or the plant according to claim 1, wherein the microorganism or the plant further produces at least one of echinenone, canthaxanthin, 3-hydroxyechinone, 3'-hydroxyechinone, adonirubin, and adonixanthin as an intermediate.

8. The method for preparing astaxanthin or an ester of astaxanthin according to claim 5, wherein the microorganism further produces at least one of echinenone, canthaxanthin, 3-hydroxyechinone, 3'-hydroxyechinone, adonirubin, and adonixanthin as an intermediate.

9. The method for preparing astaxanthin or an ester of astaxanthin according to claim 6, wherein the plant further produces at least one of echinenone, canthaxanthin, 3-hydroxyechinone, 3'-hydroxyechinone, adonirubin, and adonixanthin as an intermediate.

\* \* \* \* \*

SEQUENCE LISTING

```
<160> NUMBER OF SEQ ID NOS: 20

<210> SEQ ID NO 1
<211> LENGTH: 735
<212> TYPE: DNA
<213> ORGANISM: Brevundimonas sp.
<220> FEATURE:
<221> NAME/KEY: CDS
<222> LOCATION: (1)..(732)
```

```
<400> SEQUENCE: 1 atg acc gcc gcc gtc gcc gag ccc cgc atc gtc ccg cgc cag acc tgg        48
Met Thr Ala Ala Val Ala Glu Pro Arg Ile Val Pro Arg Gln Thr Trp
1               5                   10                  15 atc ggt ctg acc ctg gcg gga atg atc gtg gcg gga tgg ggg agc ctg        96
Ile Gly Leu Thr Leu Ala Gly Met Ile Val Ala Gly Trp Gly Ser Leu
            20                  25                  30 cac gtc tac ggc gtc tat ttt cac cgc tgg ggc acc tcc agt ctg gtg       144
His Val Tyr Gly Val Tyr Phe His Arg Trp Gly Thr Ser Ser Leu Val
        35                  40                  45 atc gtc ccg gcg atc gta gcg gtc cag acc tgg ttg tcg gtc ggc ctt       192
Ile Val Pro Ala Ile Val Ala Val Gln Thr Trp Leu Ser Val Gly Leu
    50                  55                  60 ttc atc gtc gcc cat gac gcc atg cac ggc tcc ctg gcg ccg gga cgg       240
Phe Ile Val Ala His Asp Ala Met His Gly Ser Leu Ala Pro Gly Arg
65                  70                  75                  80 ccg cgg ctg aac gcc gca gtc ggc cgg ctg acc ctg ggg ctc tat gcg       288
Pro Arg Leu Asn Ala Ala Val Gly Arg Leu Thr Leu Gly Leu Tyr Ala
                85                  90                  95 ggc ttc cgc ttc gat cgg ctg aag acg gcg cac cac gcc cac cac gcc       336
Gly Phe Arg Phe Asp Arg Leu Lys Thr Ala His His Ala His His Ala
            100                 105                 110 gcg ccc ggc acg gcc gac gac ccg gac ttt tac gcc ccg gcg ccc cgc       384
Ala Pro Gly Thr Ala Asp Asp Pro Asp Phe Tyr Ala Pro Ala Pro Arg
        115                 120                 125 gcc ttc ctt ccc tgg ttc ctg aac ttc ttt cgc acc tat ttc ggc tgg       432
Ala Phe Leu Pro Trp Phe Leu Asn Phe Phe Arg Thr Tyr Phe Gly Trp
    130                 135                 140 cgc gag atg gcg gtc ctg acc gcc ctg gtc ctg atc gcc ctc ttc ggc       480
Arg Glu Met Ala Val Leu Thr Ala Leu Val Leu Ile Ala Leu Phe Gly
145                 150                 155                 160 ctg ggg gcg cgg ccg gcc aat ctc ctg acc ttc tgg gcc gcg ccg gcc       528
Leu Gly Ala Arg Pro Ala Asn Leu Leu Thr Phe Trp Ala Ala Pro Ala
                165                 170                 175 ctg ctt tca gcg ctt cag ctc ttc acc ttc ggc acc tgg ctg ccg cac       576
Leu Leu Ser Ala Leu Gln Leu Phe Thr Phe Gly Thr Trp Leu Pro His
            180                 185                 190 cgc cac acc gac cag ccg ttc gcc gac gcc cac cac gcc cgc agc agc       624
Arg His Thr Asp Gln Pro Phe Ala Asp Ala His His Ala Arg Ser Ser
        195                 200                 205 ggc tac ggc ccc gtt ctt tcc ctg ctc acc tgc ttc cac ttc ggc cgc       672
Gly Tyr Gly Pro Val Leu Ser Leu Leu Thr Cys Phe His Phe Gly Arg
    210                 215                 220 cac cac gaa cac cac ctc acc ccc tgg cgg ccc tgg tgg cgt ttg tgg       720
His His Glu His His Leu Thr Pro Trp Arg Pro Trp Trp Arg Leu Trp
225                 230                 235                 240 cgc ggc gag tct tga                                                   735
Arg Gly Glu Ser <210> SEQ ID NO 2
<211> LENGTH: 244
<212> TYPE: PRT
<213> ORGANISM: Brevundimonas sp.

<400> SEQUENCE: 2

Met Thr Ala Ala Val Ala Glu Pro Arg Ile Val Pro Arg Gln Thr Trp
1               5                   10                  15

Ile Gly Leu Thr Leu Ala Gly Met Ile Val Ala Gly Trp Gly Ser Leu
            20                  25                  30

His Val Tyr Gly Val Tyr Phe His Arg Trp Gly Thr Ser Ser Leu Val
```

```
                35                  40                  45
Ile Val Pro Ala Ile Val Ala Val Gln Thr Trp Leu Ser Val Gly Leu
 50                  55                  60
Phe Ile Val Ala His Asp Ala Met His Gly Ser Leu Ala Pro Gly Arg
 65                  70                  75                  80
Pro Arg Leu Asn Ala Ala Val Gly Arg Leu Thr Gly Leu Tyr Ala
                 85                  90                  95
Gly Phe Arg Phe Asp Arg Leu Lys Thr Ala His Ala His His Ala
                100                 105                 110
Ala Pro Gly Thr Ala Asp Asp Pro Asp Phe Tyr Ala Pro Ala Pro Arg
                115                 120                 125
Ala Phe Leu Pro Trp Phe Leu Asn Phe Phe Arg Thr Tyr Phe Gly Trp
130                 135                 140
Arg Glu Met Ala Val Leu Thr Ala Leu Val Leu Ile Ala Leu Phe Gly
145                 150                 155                 160
Leu Gly Ala Arg Pro Ala Asn Leu Leu Thr Phe Trp Ala Ala Pro Ala
                165                 170                 175
Leu Leu Ser Ala Leu Gln Leu Phe Thr Phe Gly Thr Trp Leu Pro His
                180                 185                 190
Arg His Thr Asp Gln Pro Phe Ala Asp Ala His His Ala Arg Ser Ser
                195                 200                 205
Gly Tyr Gly Pro Val Leu Ser Leu Leu Thr Cys Phe His Phe Gly Arg
210                 215                 220
His His Glu His His Leu Thr Pro Trp Arg Pro Trp Trp Arg Leu Trp
225                 230                 235                 240
Arg Gly Glu Ser

<210> SEQ ID NO 3
<211> LENGTH: 26
<212> TYPE: DNA
<213> ORGANISM: Artificial Sequence
<220> FEATURE:
<223> OTHER INFORMATION: Synthetic primer

<400> SEQUENCE: 3
tacgaattcg atgaccgccg ccgtcg                                        26

<210> SEQ ID NO 4
<211> LENGTH: 31
<212> TYPE: DNA
<213> ORGANISM: Artificial Sequence
<220> FEATURE:
<223> OTHER INFORMATION: Synthetic primer

<400> SEQUENCE: 4
tagaggatcc tcaagactcg ccgcgccaca a                                  31

<210> SEQ ID NO 5
<211> LENGTH: 26
<212> TYPE: DNA
<213> ORGANISM: Artificial Sequence
<220> FEATURE:
<223> OTHER INFORMATION: Synthetic primer

<400> SEQUENCE: 5
tacgaattcg atgtccggac ggaagc                                        26

<210> SEQ ID NO 6
<211> LENGTH: 27
<212> TYPE: DNA
```

-continued

<210> SEQ ID NO 6
<211> LENGTH: 27
<212> TYPE: DNA
<213> ORGANISM: Artificial Sequence
<220> FEATURE:
<223> OTHER INFORMATION: Synthetic primer

<400> SEQUENCE: 6
tagaggatcc tcatgcgcgg cctccgg                                              27

<210> SEQ ID NO 7
<211> LENGTH: 26
<212> TYPE: DNA
<213> ORGANISM: Artificial Sequence
<220> FEATURE:
<223> OTHER INFORMATION: Synthetic primer

<400> SEQUENCE: 7
tacgaattcg atgagcgcac atgccc                                               26

<210> SEQ ID NO 8
<211> LENGTH: 27
<212> TYPE: DNA
<213> ORGANISM: Artificial Sequence
<220> FEATURE:
<223> OTHER INFORMATION: Synthetic primer

<400> SEQUENCE: 8
tagaggatcc tcatgcggtg tccccct                                              27

<210> SEQ ID NO 9
<211> LENGTH: 486
<212> TYPE: DNA
<213> ORGANISM: Brevundimonas sp.
<220> FEATURE:
<221> NAME/KEY: CDS
<222> LOCATION: (1)..(483)

<400> SEQUENCE: 9

```
atg gcc tgg ctg acg tgg atc gcg ctg ttc ctg acc gcc ttt ttg ggc        48
Met Ala Trp Leu Thr Trp Ile Ala Leu Phe Leu Thr Ala Phe Leu Gly
1               5                   10                  15 atg gag gcg ttc gcc tgg atc atg cac cgc tat gtg atg cac ggt ttc        96
Met Glu Ala Phe Ala Trp Ile Met His Arg Tyr Val Met His Gly Phe
            20                  25                  30 ctg tgg tcc tgg cac cgc agc cat cat gag ccg cac gat cac ccc ctg       144
Leu Trp Ser Trp His Arg Ser His His Glu Pro His Asp His Pro Leu
        35                  40                  45 gag aag aac gac ctg ttc gcc gtg gtc ttc gcc gcc ccg gcc atc gtc       192
Glu Lys Asn Asp Leu Phe Ala Val Val Phe Ala Ala Pro Ala Ile Val
    50                  55                  60 atg gtg gcc gtg ggt ctg cac ctg tgg ccc tgg gcc ctg ccg gtc ggc       240
Met Val Ala Val Gly Leu His Leu Trp Pro Trp Ala Leu Pro Val Gly
65                  70                  75                  80 ctg ggg atc acg gcc tat ggg atg gtc tat ttc ttc ttc cac gac ggc       288
Leu Gly Ile Thr Ala Tyr Gly Met Val Tyr Phe Phe Phe His Asp Gly
                85                  90                  95 ctg gtg cac cgg cgg ttc ccg acg ggc ttt tcc ggg cgg tcc ggc ttc       336
Leu Val His Arg Arg Phe Pro Thr Gly Phe Ser Gly Arg Ser Gly Phe
            100                 105                 110 tgg acg cgg cgc atc cag gcg cac cgt ctg cat cac gcc gtg cgc acg       384
Trp Thr Arg Arg Ile Gln Ala His Arg Leu His His Ala Val Arg Thr
        115                 120                 125 cgc gaa ggc tgc gtc tcc ttc ggc ttt ctg tgg gtg cgg tcg gcg cgg       432
Arg Glu Gly Cys Val Ser Phe Gly Phe Leu Trp Val Arg Ser Ala Arg
    130                 135                 140 gcg ctg aag gcc gaa ctg gct cag aag cgg ggc tct tcc agc agc ggc       480
Ala Leu Lys Ala Glu Leu Ala Gln Lys Arg Gly Ser Ser Ser Ser Gly
```

Ala Leu Lys Ala Glu Leu Ala Gln Lys Arg Gly Ser Ser Ser Gly
145                 150                 155                 160 gcc tga                                                                486
Ala

<210> SEQ ID NO 10
<211> LENGTH: 161
<212> TYPE: PRT
<213> ORGANISM: Brevundimonas sp.

<400> SEQUENCE: 10

Met Ala Trp Leu Thr Trp Ile Ala Leu Phe Leu Thr Ala Phe Leu Gly
1               5                   10                  15

Met Glu Ala Phe Ala Trp Ile Met His Arg Tyr Val Met His Gly Phe
            20                  25                  30

Leu Trp Ser Trp His Arg Ser His Glu Pro His Asp His Pro Leu
        35                  40                  45

Glu Lys Asn Asp Leu Phe Ala Val Val Phe Ala Ala Pro Ala Ile Val
    50                  55                  60

Met Val Ala Val Gly Leu His Leu Trp Pro Trp Ala Leu Pro Val Gly
65                  70                  75                  80

Leu Gly Ile Thr Ala Tyr Gly Met Val Tyr Phe Phe His Asp Gly
                85                  90                  95

Leu Val His Arg Arg Phe Pro Thr Gly Phe Ser Gly Arg Ser Gly Phe
            100                 105                 110

Trp Thr Arg Arg Ile Gln Ala His Arg Leu His His Ala Val Arg Thr
        115                 120                 125

Arg Glu Gly Cys Val Ser Phe Gly Phe Leu Trp Val Arg Ser Ala Arg
    130                 135                 140

Ala Leu Lys Ala Glu Leu Ala Gln Lys Arg Gly Ser Ser Ser Gly
145                 150                 155                 160

Ala

<210> SEQ ID NO 11
<211> LENGTH: 26
<212> TYPE: DNA
<213> ORGANISM: Artificial Sequence
<220> FEATURE:
<223> OTHER INFORMATION: Synthetic primer

<400> SEQUENCE: 11
tacgaattcg atggcctggc tgacgt                                           26

<210> SEQ ID NO 12
<211> LENGTH: 27
<212> TYPE: DNA
<213> ORGANISM: Artificial Sequence
<220> FEATURE:
<223> OTHER INFORMATION: Synthetic primer

<400> SEQUENCE: 12
tagaggatcc tcaggcgccg ctgctgg                                          27

<210> SEQ ID NO 13
<211> LENGTH: 26
<212> TYPE: DNA
<213> ORGANISM: Artificial Sequence
<220> FEATURE:
<223> OTHER INFORMATION: Synthetic primer

<400> SEQUENCE: 13
tacgaattcg atgttgtgga tttgga    26

<210> SEQ ID NO 14
<211> LENGTH: 27
<212> TYPE: DNA
<213> ORGANISM: Artificial Sequence
<220> FEATURE:
<223> OTHER INFORMATION: Synthetic primer

<400> SEQUENCE: 14
tagaggatcc ttacttcccg gatgcgg    27

<210> SEQ ID NO 15
<211> LENGTH: 26
<212> TYPE: DNA
<213> ORGANISM: Artificial Sequence
<220> FEATURE:
<223> OTHER INFORMATION: Synthetic primer

<400> SEQUENCE: 15
tacgaattcg atgacgcaat tcctca    26

<210> SEQ ID NO 16
<211> LENGTH: 27
<212> TYPE: DNA
<213> ORGANISM: Artificial Sequence
<220> FEATURE:
<223> OTHER INFORMATION: Synthetic primer

<400> SEQUENCE: 16
tagaggatcc tcacgacgga cgctcgt    27

<210> SEQ ID NO 17
<211> LENGTH: 26
<212> TYPE: DNA
<213> ORGANISM: Artificial Sequence
<220> FEATURE:
<223> OTHER INFORMATION: Synthetic primer

<400> SEQUENCE: 17
tacgaattcg atgaccaatt tcctga    26

<210> SEQ ID NO 18
<211> LENGTH: 27
<212> TYPE: DNA
<213> ORGANISM: Artificial Sequence
<220> FEATURE:
<223> OTHER INFORMATION: Synthetic primer

<400> SEQUENCE: 18
tagaggatcc tcacgtgcgc tcctgcg    27

<210> SEQ ID NO 19
<211> LENGTH: 26
<212> TYPE: DNA
<213> ORGANISM: Artificial Sequence
<220> FEATURE:
<223> OTHER INFORMATION: Synthetic primer

<400> SEQUENCE: 19
ttcccgggga atggaaatag ttctct    26

<210> SEQ ID NO 20
<211> LENGTH: 27

```
<212> TYPE: DNA
<213> ORGANISM: Artificial Sequence
<220> FEATURE:
<223> OTHER INFORMATION: Synthetic primer

<400> SEQUENCE: 20
tgccaagctt ttatttgaaa tacttga                                              27
```